US010463633B2

(12) United States Patent
Desai

(10) Patent No.: US 10,463,633 B2
(45) Date of Patent: *Nov. 5, 2019

(54) THERAPEUTIC FORMULATION FOR REDUCED DRUG SIDE EFFECTS

(75) Inventor: Subhash Desai, Wilmette, IL (US)

(73) Assignee: KemPharm, Inc., Celebration, FL (US)

( * ) Notice: Subject to any disclaimer, the term of this patent is extended or adjusted under 35 U.S.C. 154(b) by 338 days.

This patent is subject to a terminal disclaimer.

(21) Appl. No.: 13/093,662

(22) Filed: Apr. 25, 2011

(65) Prior Publication Data

US 2011/0262496 A1 Oct. 27, 2011

Related U.S. Application Data

(60) Provisional application No. 61/369,338, filed on Jul. 30, 2010, provisional application No. 61/327,486, filed on Apr. 23, 2010.

(51) Int. Cl.
| A61P 25/26 | (2006.01) |
| A61K 31/137 | (2006.01) |
| A61K 31/135 | (2006.01) |
| A61K 31/165 | (2006.01) |
| A61K 31/4168 | (2006.01) |
| A61K 9/14 | (2006.01) |
| A61K 9/19 | (2006.01) |
| A61K 9/48 | (2006.01) |

(52) U.S. Cl.
CPC .............. *A61K 31/137* (2013.01); *A61K 9/14* (2013.01); *A61K 9/19* (2013.01); *A61K 9/4866* (2013.01); *A61K 31/135* (2013.01); *A61K 31/165* (2013.01); *A61K 31/4168* (2013.01); *Y10T 428/2982* (2015.01)

(58) Field of Classification Search
CPC .............................. A61P 25/26; A61K 31/137
See application file for complete search history.

(56) References Cited

U.S. PATENT DOCUMENTS

| 5,145,648 | A | | 9/1992 | Miyahara et al. |
| 5,213,808 | A | * | 5/1993 | Bar-Shalom et al. ........ 424/473 |
| 5,470,583 | A | | 11/1995 | Na et al. |
| 5,510,118 | A | | 4/1996 | Bosch et al. |
| 5,518,187 | A | | 5/1996 | Bruno et al. |
| 5,518,738 | A | | 5/1996 | Eickhoff et al. |
| 5,534,270 | A | | 7/1996 | De Castro |
| 5,543,133 | A | | 8/1996 | Swanson et al. |
| 5,560,932 | A | | 10/1996 | Bagchi et al. |
| 5,585,108 | A | | 12/1996 | Ruddy et al. |
| 5,641,515 | A | | 6/1997 | Ramtoola |
| 5,662,883 | A | | 9/1997 | Bagchi et al. |
| 5,665,331 | A | | 9/1997 | Bagchi et al. |
| 5,718,388 | A | | 2/1998 | Czekai et al. |
| 5,862,999 | A | | 1/1999 | Czekai et al. |
| 6,322,819 | B1 | * | 11/2001 | Burnside et al. ............. 424/494 |
| 6,375,986 | B1 | | 4/2002 | Ryde et al. |
| 6,592,903 | B2 | | 7/2003 | Ryde et al. |
| 6,913,768 | B2 | | 6/2005 | Couch et al. |
| 6,976,647 | B2 | | 12/2005 | Reed et al. |
| 7,198,795 | B2 | | 4/2007 | Cooper et al. |
| 7,399,488 | B2 | | 7/2008 | Hirsh et al. |
| 7,476,402 | B2 | | 1/2009 | Kumar et al. |
| 7,510,726 | B2 | | 3/2009 | Kumar et al. |
| 9,511,037 | B2 | * | 12/2016 | Desai ................... A61K 31/137 |
| 2002/0034474 | A1 | * | 3/2002 | Sabel ................... A61K 9/5138 424/1.25 |
| 2002/0044962 | A1 | * | 4/2002 | Cherukuri et al. ........... 424/459 |
| 2002/0102294 | A1 | | 8/2002 | Bosch et al. |
| 2003/0077297 | A1 | * | 4/2003 | Chen et al. ................... 424/400 |
| 2004/0220277 | A1 | * | 11/2004 | Couch et al. ................. 514/649 |
| 2005/0152974 | A1 | | 7/2005 | Boehm et al. |
| 2006/0057206 | A1 | | 3/2006 | Wong et al. |
| 2006/0147496 | A1 | | 7/2006 | Lin et al. |
| 2007/0219201 | A1 | | 9/2007 | Carroll, Jr. et al. |
| 2007/0264323 | A1 | | 11/2007 | Shojaei et al. |
| 2008/0026053 | A1 | | 1/2008 | Dixit |
| 2009/0297617 | A1 | | 12/2009 | Rariy et al. |
| 2011/0065796 | A1 | | 3/2011 | Whomsley et al. |
| 2013/0039960 | A1 | | 2/2013 | Desai |
| 2017/0105983 | A1 | | 4/2017 | Desai |

FOREIGN PATENT DOCUMENTS

| WO | 2004/071501 | 8/2004 |
| WO | 2011133980 | 10/2011 |
| WO | 2011156710 A2 | 12/2011 |

OTHER PUBLICATIONS

Wilens et al. (The Psychiatric Clinics of North America: Pediatric Psychopharmacology; Mar. 1992; 15(1):191-222).*
Gabbard, Glen O. Gabbard's treatments of psychiatric disorders. American Psychiatric Publishing Inc. Arlington, VA. 2007.*
D.J. Begley (Pharmacology & Therapeutics 104 (2004) 29-45).*
Hans et al., "Nanoparticles for drug delivery." Handbook of Nanoscience, Engineering, and Technology. Second Edition. Gerald. Boca Raton, FL; Taylor & Francis Group, 2007.*
Posey et al. (CNS Drug Reviews; "Guanfacine and Guanfacine Extended Release:Treatment for ADHD and Related Disorders." CNS Drug Rev. 2007 Winter;13(4):465-74). (Year: 2007).*
Agarwal et al.; 2008; "Combination of Atomoxetine and Methylphenidate in Attention Deficit/Hyperactivity Disorder: A Case Report." J Can Acad Child Adolesc Psychiatry, 17(3): 160.
clincaltrials.gov; 2008; "Single Versus Combination Medication Treatment for Children With Attention Deficit Hyperactivity Disorder"; National Institute of Mental Health (NIMH); retrieved Apr. 19, 2010 from http://clinicaltrials.gov/ct2/show/NCT00429273.
Jay; 2010; "Combination Therapy with Shire's Intuniv Shown Safe for Non-responsive ADHD Patients or Those with Sleep Problems"; Mental Health Behavioral Health Medical Professionals Resources; retrieved Apr. 19, 2010 from http://www.behavioralhealthcentral.com/index.php/20100120187285/Sleep-latest/combination-t.

(Continued)

Primary Examiner — Rachael E Bredefeld
Assistant Examiner — Chris E Simmons
(74) Attorney, Agent, or Firm — McAndrews, Held & Malloy, Ltd.

(57) ABSTRACT

The present invention provides drug therapy formulations for reducing the side effects associated with a therapeutic. In some embodiments, the present invention provides a reduction in sleep- and diet-related side effects associated with a therapeutic.

6 Claims, 17 Drawing Sheets

(56) References Cited

OTHER PUBLICATIONS

Shire Press Release; 2009; "Shire Announces Publication of Open-Label Study on Coadministration of INTUNIV™ (guanfacine) Extended-Release Tablets with Stimulants".

Sallee; 2008; "The Role of Alpha 2 Agonists in the Attention Deficit/Hyperactivity Disorder Treatment Paradigm"; Medscape Psychiatry & Mental Health; retrieved Apr. 19, 2010 from http://cme.medscape.com/viewarticle/577743.

Spencer et al.; 2009; "Safety and Effectiveness of Coadministration of Guanfacine Extended Release and Psychostimulants in Children and Adolescents with Attention-Deficit=Hyperactivity Disorder"; Journal of Child and Adolescent Psychopharmacology; 19(5): 501-510.

Ravikumar et al.; 2009; "Formation of Nanoparticles of Water-soluble Molecules through Evaporation of Water-in-Oil Microemulsions"; RSS 2009, Dept. of Chemical Engg, IIT Bombay; Oral Presentations.

Bawa; 2008; "Nanoparticle-based Therapeutics in Humans: A Survey"; Nanotechnology Law & Business.

Castellanos FX et al. "Controlled stimulant treatment of ADHD and comorbid Tourette's syndrome: effects of stimulant and dose." J Am Acad Child Adolesc Psychiatry. May 1997; 36(5):589-96.

Bloch et al., "Meta-analysis: treatment of attention-deficit/hyperactivity disorder in children with comorbid tic disorders." J Am Acad Child Adolesc Psychiatry. Sep. 2009;48(9):884-93.

Scahill et al., "A Placebo-Controlled Study of Guanfacine in the Treatment of Children with Tic Disorders and Attention Deficit Hyperactivity Disorder." Am J. Psychiatry 2001, 158:1067-1074.

Dextroamphetamine Compound Summary—PubChem—CID #5826, Sep. 16, 2004, pp. 1-14.

Dexedrine FDA Label, Prescribing Information, GlaxoSmithKline 2007, pp. 1-11.

Adderall FDA Label, DSM Pharmaceuticals Inc., Mar. 2007, pp. 1-15.

The Tourette's Syndrome Study Group "Treatment of ADHD in children with tics: A randomized controlled trial" Neurology 2002; 58:527-536.

Kurlan et al., "Clonidine and methylphenidate were effective for attention deficit hyperactivity disorder in children with comorbid tics." Evidence-based Medicine, Sep. 2002, 7(5): 157.

Hans, et al., "Biodegradable nanoparticles for drug delivery and targeting" Current Opinion in Solid State and Materials Science, 2002, 6:319-32.

Junghanns et al., "Nanocrystal technology, drug delivery and clinical applications." Int J Nanomedicine. 2008;3(3):295-309.

Brown et al., "Atomoxetine and stimulants in combination for treatment of attention deficit hyperactivity disorder: four case reports." J Child Adolesc Psychopharmacol. 2004 Spring;14(1):129-36.

Di and Kerns, "Drug-Like Properties: Concepts, structure, design and methods," ISBN: 978-0-12-801076-1, Elsevier, chapters 8 and 9, (2016).

Advisory Action in U.S. Appl. No. 13/656,415 dated Sep. 22, 2015.
Office Action in U.S. Appl. No. 13/656,415 dated Mar. 28, 2014.
Office Action in U.S. Appl. No. 13/656,415 dated Jun. 24, 2015.
Office Action in U.S. Appl. No. 13/656,415 dated Sep. 5, 2013.
Office Action in U.S. Appl. No. 13/656,415 dated Jan. 7, 2015.
Notice of Allowance in U.S. Appl. No. 13/656,415 dated Sep. 23, 2016.
Office Action in U.S. Appl. No. 13/656,415 dated May 28, 2013.
Office Action in U.S. Appl. No. 15/339,453 dated Nov. 6, 2017.
Office Action in U.S. Appl. No. 15/339,453 dated Apr. 24, 2017.
European Patent Office, "Intention to Grant," issued in connection with European Patent Application No. 11772852.7, dated Jan. 26, 2018.

* cited by examiner

THERAPEUTIC FORMULATION FOR REDUCED DRUG SIDE EFFECTS

This application claims priority to provisional patent application Ser. No. 61/327,486, filed Apr. 23, 2010 and provisional patent application Ser. No. 61/369,338 filed Jul. 30, 2010 which is herein incorporated by reference in its entirety.

FIELD OF THE INVENTION

The present invention provides drug therapy formulations for reducing the side effects associated with a therapeutic. In some embodiments, the present invention provides a reduction in sleep- and diet-related side effects associated with a therapeutic.

BACKGROUND

Drug side effects, including difficulty sleeping, loss of appetite, and abdominal pain, are a significant medical issue. Insomnia, difficulty falling asleep, or difficulty remaining asleep can result in problem sleepiness, which impairs the health, quality of life and safety of those affected. Appetite disorders, such as loss of appetite, can cause reduced energy, health, quality of life, and can cause additional downstream nutritional deficiencies. Abdominal pain can greatly reduce the quality of life for a patient, and greatly reduce compliance with a therapy regimen. Drug side effects often become more pronounced as drug dosages are increased to achieve longer lasting benefits. As a result, there is a need for therapies which achieve long lasting without the associated side effects.

For example, attention deficit hyperactive disorder (ADHD) is commonly treated with stimulants (e.g. norepinephrine reuptake inhibitors (e.g. amphetamines, methylphenidate, etc.)). In order to provide sufficient therapeutic benefit throughout the day, a large dose morning dose is commonly administered. Such large doses of stimulants are frequently associated with significant side effects, including insomnia, abdominal pain, and loss of appetite. Children, who commonly suffer from ADHD, are particularly susceptible to disruption of sleep and/or eating habits and the additional downstream consequences thereof.

SUMMARY OF THE INVENTION

In some embodiments, the present invention provides a pharmaceutical composition comprising a stimulant pharmacologic agent (e.g., agent for treatment of ADHD or other psychiatric conditions) and a non-stimulant pharmacologic agent for treatment of ADHD (e.g., agent for treatment of ADHD or other psychiatric conditions), wherein the stimulant pharmacologic agent and the non-stimulant pharmacologic agent are formulated for release according to separate schedules. In some embodiments, the stimulant pharmacologic agent is formulated to begin release upon administration to a subject. In some embodiments, the stimulant pharmacologic agent is formulated to release over the course of 0.15 (or less) to 6 hours (e.g., 0.15-6 hours, 0.1-5 hours, 0.15-2 hours, 0.15-3 hours, 0.15-4 hours, 0.5-6 hours, etc.), although the invention is not limited to this particular range. In some embodiments, all or a portion of the stimulant pharmaceutical agent is coated for enteric release. In some embodiments, the non-stimulant pharmacologic agent is formulated to release over the course of 0.15 to 14 (e.g., 0.15-14 hours, 0.3-14 hours, 0.3-12 hours, 0.5-10 hours, 0.5-14 hours, 0.15-8 hours, etc.), although the invention is not limited to this particular range. In some embodiments, the non-stimulant pharmacologic agent is formulated to begin release upon administration to a subject. In some embodiments, the non-stimulant pharmacologic agent is formulated for delayed release. In some embodiments, delayed release comprises release beginning 3 to 6 hours after administration to a subject. In some embodiments, all or a portion of the non-stimulant pharmaceutical agent is coated for enteric release. In some such embodiments, after an enteric coating is removed, the non-stimulant is immediately released. In some embodiments, a pharmaceutical composition further comprises an agent to reduce abdominal pain. In some embodiments, the agent to reduce abdominal pain is coated for enteric release. In some embodiments, the agent to reduce abdominal pain comprises peppermint oil.

In some embodiments, the present invention provides a pharmaceutical composition comprising a stimulant pharmacologic agent for treatment of ADHD, wherein the stimulant pharmacologic agent is provided in a nanoparticulate formulation (e.g. for enhanced bioavailabilty, fast action, for controlled release, etc.). In some embodiments, the present invention provides a pharmaceutical composition comprising a non-stimulant pharmacologic agent for treatment of ADHD, wherein the non-stimulant pharmacologic agent is provided in a nanoparticulate formulation (e.g. for enhanced bioavailabilty, for controlled release, etc.). In some embodiments, the present invention provides a pharmaceutical composition comprising a stimulant pharmacologic agent for treatment of ADHD and a non-stimulant pharmacologic agent for treatment of ADHD, wherein the stimulant pharmacologic agent is provided in a nanoparticulate formulation, wherein the non-stimulant pharmacologic agent is provided in a nanoparticulate formulation, or wherein both the stimulant pharmacologic agent and non-stimulant pharmacologic agent are provided in a nanoparticulate formulation, and wherein the stimulant pharmacologic agent and the non-stimulant pharmacologic agent are formulated for release according to separate schedules. In one or more pharmacologic agents administered in a nanoparticulate formulation are further formulated for administration via other formulation methods described herein (e.g. co-administration, enteric coating, controlled release, delayed release, immediate release, etc.). In some embodiments, a stimulant pharmacologic agent and/or non-stimulant pharmacologic agent is complexed to one or more compounds comprising a nanoparticle (e.g. to enhance bioavailablity, to provide slower release of therapeutic, etc.). In some embodiments, a stimulant pharmacologic agents and/or non-stimulant pharmacologic agents are encapsulated within nanoparticles. It is contemplated that use of nanoparticulate formulations permits further reduction in the dosage of one or more active agents to achieve an efficacious dose with fewer or reduced side effects.

In some embodiments, the present invention provides a pharmaceutical composition comprising a first pharmacologic agent (e.g., stimulant) and a second pharmaceutical agent, wherein the first pharmaceutical agent is formulated as a nanoparticulate and the second pharmaceutical agent is not formulated as a nanoparticulate. In some embodiments, the first pharmacologic agent is a stimulant and the second pharmaceutical agent is a non-stimulant. In some embodiments, the first pharmacologic agent is a stimulant and the second pharmaceutical agent is a stimulant. In some embodiments, the first pharmacologic agent is a non-stimulant and the second pharmaceutical agent is a non-stimulant. In some embodiments, the first pharmacologic agent and the second pharmaceutical agent are the same agents (e.g., same pharmaceutical compounds). In some embodiments, the first pharmacologic agent and the second pharmaceutical agent are formulated differently (e.g., nanoparticulate formulation, slow-release formulation, etc.).

In some embodiments, the present invention provides a pharmaceutical composition comprising a first pharmaceutical formulation and a second pharmaceutical formulation, wherein the first pharmaceutical formulation comprises one or more pharmaceutical agents formulated as a nanoparticulate, and the a second pharmaceutical formulation comprises one or more pharmaceutical agents formulated for slow-release. In some embodiments, the first pharmaceutical formulation and second pharmaceutical formulation comprise the same pharmaceutical agents. In some embodiments, the first pharmaceutical formulation and second pharmaceutical formulation comprise the different pharmaceutical agents. In some embodiments, the first pharmaceutical formulation comprises one or more stimulant pharmaceuticals. In some embodiments, the first pharmaceutical formulation comprises one or more non-stimulant pharmaceuticals. In some embodiments, the second pharmaceutical formulation comprises one or more stimulant pharmaceuticals. In some embodiments, the second pharmaceutical formulation comprises one or more non-stimulant pharmaceuticals. In some embodiments, the pharmaceutical agents in the first formulation are formulated for rapid-release upon administration to a subject. In some embodiments, the pharmaceutical agents in the second formulation are formulated for slow-release upon administration to a subject.

In some embodiments, the present invention provides a pharmaceutical composition comprising a stimulant pharmaceutical agent formulated as a nanoparticulate. In some embodiments, the formulation permits fast action of the stimulant (e.g., biological activity in less than 15 minutes, less than 10 minutes, less than 5 minutes, less than 2 minutes) and/or such that activity (and associated side effects, such as sleeplessness) are diminished after a desirable period of time (e.g., before, for example, 10 hours, 8 hours, 6 hours, or 4 hours after administration).

In some embodiments, the present invention provides nanoparticle compositions comprising one or more pharmaceutical agents (e.g., stimulant, non-stimulant, etc.). In some embodiments, pharmaceutical nanoparticulates have a diameter (e.g., mean diameter) of less than about 10 μm (e.g., <10 μm, <5 μm, <2 μm, <1 μm, <500 nm, <200 nm, <100 nm, <50 nm, <20 nm, <10 nm, etc.). In some embodiments, a plurality of pharmaceutical nanoparticulates have a mean diameter of less than about 10 μm (e.g., <10 μm, <5 μm, <2 μm, <1 μm, <500 nm, <200 nm, <100 nm, <50 nm, <20 nm, <10 nm, etc.). In some embodiments, pharmaceutical nanoparticulates have a diameter (e.g., mean diameter) of about 500 nm. In some embodiments, pharmaceutical nanoparticulates have a diameter (e.g., mean diameter) of about 400 nm. In some embodiments, pharmaceutical nanoparticulates have a diameter (e.g., mean diameter) of about 300 nm. In some embodiments, pharmaceutical nanoparticulates have a diameter (e.g., mean diameter) of about 200 nm. In some embodiments, pharmaceutical nanoparticulates have a diameter (e.g., mean diameter) of about 100 nm. In some embodiments, pharmaceutical nanoparticulates have a diameter (e.g., mean diameter) of about 100-500 nm.

In some embodiments, methods are provided for the production of pharmaceutical nanoparticles. In some embodiments, pharmaceutical nanoparticles are produced through one or more steps, including, but not limited to milling and drying. In some embodiments, milling comprises roller milling, spindle milling, or any suitable alternative (e.g., other form of milling, alternative to milling, etc.). In some embodiments, milling of one or more pharmaceutical agents is performed in the presence of one or more solvents (e.g., milling vehicles). In some embodiments, suitable solvents for milling minimize salvation of the pharmaceutical agent(s). In some embodiments, suitable solvents for milling are volatile. In some embodiments, suitable solvents for milling include, but are not limited to ethyl acetate, methylene chloride, hexanes, and cyclomethicone. Methods of making nanoparticulate compositions are described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference. In some embodiments, drying of a pharmaceutical composition of the present invention is performed by any suitable method (e.g., air drying, vacuum drying, lyophilization, etc.). In some embodiments, milling and or drying is followed by one or more additional steps including but not limited to sonication.

In some embodiments, the present invention provides a pharmaceutical composition comprising an agent to deter abuse of said pharmaceutical composition. In some embodiments, an agent to deter abuse comprises a nasal and/or muscosal irritant, polymer composition, and/or emetic compound.

In some embodiments, the stimulant pharmaceutical agent is an agent that increases the levels of dopamine or norepinephrine in a treated subject. In some embodiments, the non-stimulant pharmaceutical agent is an α2 adrenergic agonist. Stimulant pharmacologic agents include, but are not limited to, any one or more of amphetamines (e.g., (±)-1-phenylpropan-2-amine), lisdexamphetamines (e.g., N-[(1S)-1-methyl-2-phenylethyl]-L-lysinamide), methylphenidates (e.g., methyl phenyl(piperidin-2-yl)acetate), dexmethylphenidates (e.g., (R,R)-(+)-Methyl 2-phenyl-2-(2-piperidyl) acetate), and dexamphetamines (e.g., (5)-1-phenylpropan-2-amine), or derivatives thereof. In some embodiments, the stimulant pharmacologic agent is selected from amphetamines (e.g. Adderall XR, Adderall, etc.), lisdexamphetamines (e.g. Vyvanse, etc.), methylphenidates (e.g. Concerta, Ritalin, Ritalin LA, Metadate CD, Metadate ER, etc.), dexmethylphenidates (e.g. Focalin, Focalin XR, etc.), and dexamphetamines (e.g. Dexedrine). In some embodiments, the non-stimulant pharmacologic agents include, but are not limited to, Atomoxetine ((3R)—N-methyl-3-(2-methylphenoxy)-3-phenyl-propan-1-amine; (R)—N-methyl-3-phenyl-3-(o-tolyloxy) propan-1-amine), Guanfacine (N-(diaminomethylidene)-2-(2,6-dichlorophenyl) acetamide), and Clonidine (N-(2,6-dichlorophenyl)-4,5-dihydro-1H-imidazol-2-amine) or derivatives thereof. In some embodiments, the non-stimulant pharmacologic agent is selected from Atomoxetine (e.g. Strattera, etc.), Guanfacine (e.g. Intuniv, etc.), Clonidine, etc.

In some embodiments, the present invention provides a method of treating, preventing, or ameliorating signs or symptoms of a disease or condition in a subject. To illustrate aspects of the invention, the remaining description focuses on ADHD (attention deficit hyperactivity disorder). However, it should be understood that the invention is not limited to this particular condition. In some embodiments, the present invention provides treatment and/or symptom reduction for: ADHD, one or more symptoms of ADHD, ADHD-like conditions, psychiatric conditions, conditions presenting one or more symptoms of ADHD, attention deficit disorder (ADD), bipolar disorder, autism, seizure disorders, etc. In some embodiments, the methods comprising administering to a subject suffering from ADHD a combination therapeutic agent comprising a stimulant pharmacologic agent and a non-stimulant pharmacologic agent, wherein the stimulant pharmacologic agent and the non-stimulant pharmacologic agent are formulated for release according to separate schedules, and wherein administration of the combination therapeutic agent. Such embodiments provide effective relief of symptoms of ADHD while minimizing or avoiding undesired side-effects. In some embodiments, the combination therapeutic agent provides effective relief of symptoms of ADHD using lower doses of the stimulant pharmacologic agent and/or the non-stimulant pharmacologic agent than when the stimulant pharmacologic agent or the non-stimulant pharmacologic agent are used alone to treat ADHD (i.e., the dose administered is lower than the normal recommended dose for a particular subject, taking into account age, size, gender, or other factors). In some embodiments, the combination therapeutic agent provides effective relief of symptoms of ADHD with fewer or reduced side effects from the stimulant pharmacologic agent and/or the non-stimulant pharmacologic agent than when the stimulant pharmacologic agent or the non-stimulant pharmacologic agent are used alone to treat ADHD. In some embodiments, the combination therapeutic agent provides effective relief of symptoms of ADHD for longer duration than when the stimulant pharmacologic agent or the non-stimulant pharmacologic agent are used alone to treat ADHD. In some embodiments, the stimulant pharmacologic agent is formulated to begin release upon administration to a subject. In some embodiments, the stimulant pharmacologic agent is formulated to release over the course of 0.5 to 6 hours, although other ranges may be used, as desired. In some embodiments, the non-stimulant pharmacologic agent is formulated to release over the course of 3 to 12 hours, although other ranges may be used, as desired. In some embodiments, the non-stimulant pharmacologic agent is formulated to begin release upon administration to a subject. In some embodiments, the non-stimulant pharmacologic agent is formulated for delayed release. In some embodiments, the delayed release comprises release beginning 3 to 6 hours after administration to a subject, although other ranges may be used, as desired. In some embodiments, the subject is a child (e.g., a human child under the age of 18, 16, 14, 12, 10, 8, 6, etc.). In some embodiments, the combination therapeutic agent provides effective relief of symptoms of ADHD for 8 to 16 hours. Side effects, such as problems with sleep or appetite are reduced or eliminated in the later hours of the day upon a morning administration of the agents.

In some embodiments, the present invention provides a method of treating, preventing, or ameliorating signs or symptoms of a disease or condition in a subject by administering a pharmaceutical composition to the subject. In some embodiments, the pharmaceutical agent comprises a first formulation and a second formulation. In some embodiments, the first formulation comprises a nanoparticulate of one or more pharmaceutical agents. In some embodiments, the first formulation comprises one or more pharmaceutical agents and one or more non-pharmaceutical compositions. In some embodiments, the first formulation is configured for rapid-release of one or more pharmaceutical agents upon administration to a subject. In some embodiments, the second formulation comprises one or more pharmaceutical agents. In some embodiments, the second formulation comprises one or more pharmaceutical agents and one or more non-pharmaceutical compositions. In some embodiments, the second formulation is configured for slow-release of one or more pharmaceutical agents upon administration to a subject. In some embodiments, administration of a first formulation and a second formulation reduces side effects related to one or more pharmaceutical agents administered to a subject (e.g., pharmaceutical agents in the first formulation, pharmaceutical agents in the second formulation, pharmaceutical agents in both formulations).

In some embodiments, pharmaceutical compositions comprising nanoparticulate formulations and/or non-nanoparticulate formuations areutilized in solid or liquid dosage formulations, such as liquid dispersions, gels, aerosols, ointments, creams, controlled release formulations, fast melt formulations, lyophilized formulations, tablets, capsules, rapid-release formulations, delayed release formulations, extended release formulations, pulsatile release formulations, mixed immediate release and controlled release formulations, etc.

In some embodiments, the present invention provides a pharmaceutical composition comprising a nanoparticulate formulation of l-amphetamine and d-amphetamine. In some embodiments, a pharmaceutical composition comprises a nanoparticulate formulation of Adderall. In some embodiments, the mean nanoparticle diameter of the nanoparticulate formulation is less than or approximately 500 nm. In some embodiments, the mean nanoparticle diameter of the nanoparticulate formulation is less than or approximately 250 nm.

In some embodiments, the present invention provides method of treating ADHD (or a similar psychiatric condition or a condition exhibiting similar symptoms) in a subject by administering a pharmaceutical composition comprising a nanoparticulate formulation of l-amphetamine and d-amphetamine. In some embodiments, the present invention provides method of treating ADHD (or a similar psychiatric condition or a condition exhibiting similar symptoms) in a subject by administering a pharmaceutical composition comprising a nanoparticulate formulation of Adderall. In some embodiments, the present invention provides method of treating ADHD (or a similar psychiatric condition or a condition exhibiting similar symptoms) in a subject by co-administering: (a) a pharmaceutical composition comprising a nanoparticulate formulation of l-amphetamine and d-amphetamine, and (b) a second pharmaceutical agent to the subject. In some embodiments, the present invention provides method of treating ADHD (or a similar psuchiatric condition or a condition exhibiting similar symptoms) in a subject by co-administering: (a) a pharmaceutical composition comprising a nanoparticulate formulation of Adderall, and (b) a second pharmaceutical agent to the subject. In some embodiments, the second pharmaceutical agent is formulated for delayed release. In some embodiments, the second pharmaceutical agent is coated for enteric release. In some embodiments, the second pharmaceutical agent is a non-stimulant. In some embodiments, the non-stimulant is selected from Atomoxetine, Guanfacine, and Clonidine. In some embodiments, the second pharmaceutical agent is a stimulant.

In some embodiments, the present invention provides a method for producing a nanoparticulate formulation of l-amphetamine and d-amphetamine comprising: (a) forming a mixture of l-amphetamine, d-amphetamine, and one or more vehicles; (b) milling said mixture; and (c) drying said mixture. In some embodiments, the present invention provides a method for producing a nanoparticulate formulation of Adderall comprising: (a) forming a mixture of Adderall and one or more vehicles; (b) milling said mixture; and (c) drying said mixture. In some embodiments, the nanoparticles produced have a mean nanoparticle diameter of less than 500 nm. In some embodiments, the nanoparticles produced have a mean nanoparticle diameter of less than 250 nm.

In some embodiments, the present invention provides a pharmaceutical composition comprising a first nanoparticulate formulation and a second non-nanoparticulate formulation, wherein the nanoparticulate formulation comprises one or more stimulants and the non-nanoparticulate formulation comprises one or more non-stimulant pharmaceutical agents. In some embodiments, the one or more stimulants comprise l-amphetamine and d-amphetamine. In some embodiments, the one or more stimulants comprises Adderall. In some embodiments, the mean nanoparticle diameter of the nanoparticulate formulation is less than 500 nm. In some embodiments, the mean nanoparticle diameter of the nanoparticulate formulation is less than 250 nm. In some embodiments, one of the one or more non-stimulants and selected from Atomoxetine, Guanfacine, and Clonidine

DETAILED DESCRIPTION OF THE INVENTION

Figure 1:
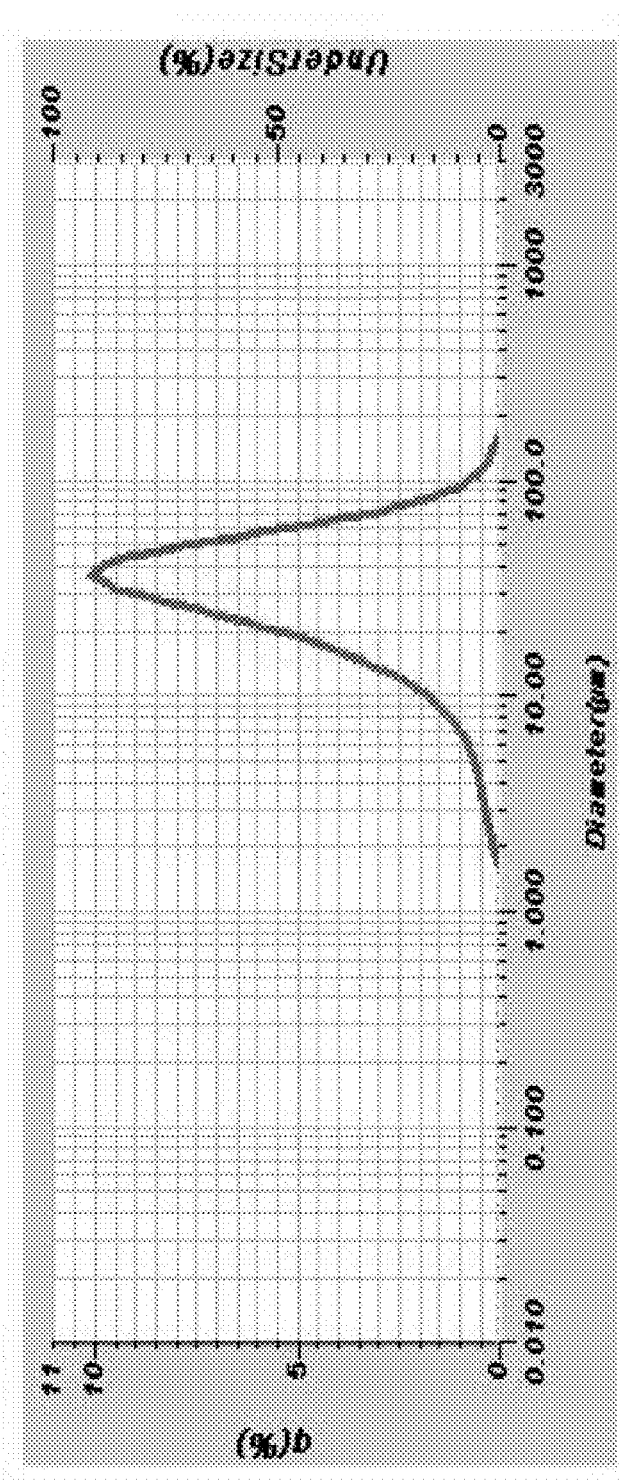
FIG. 1 shows laser scattering particle size distribution analysis of amphetamine salts prior to milling.
Figure 2:
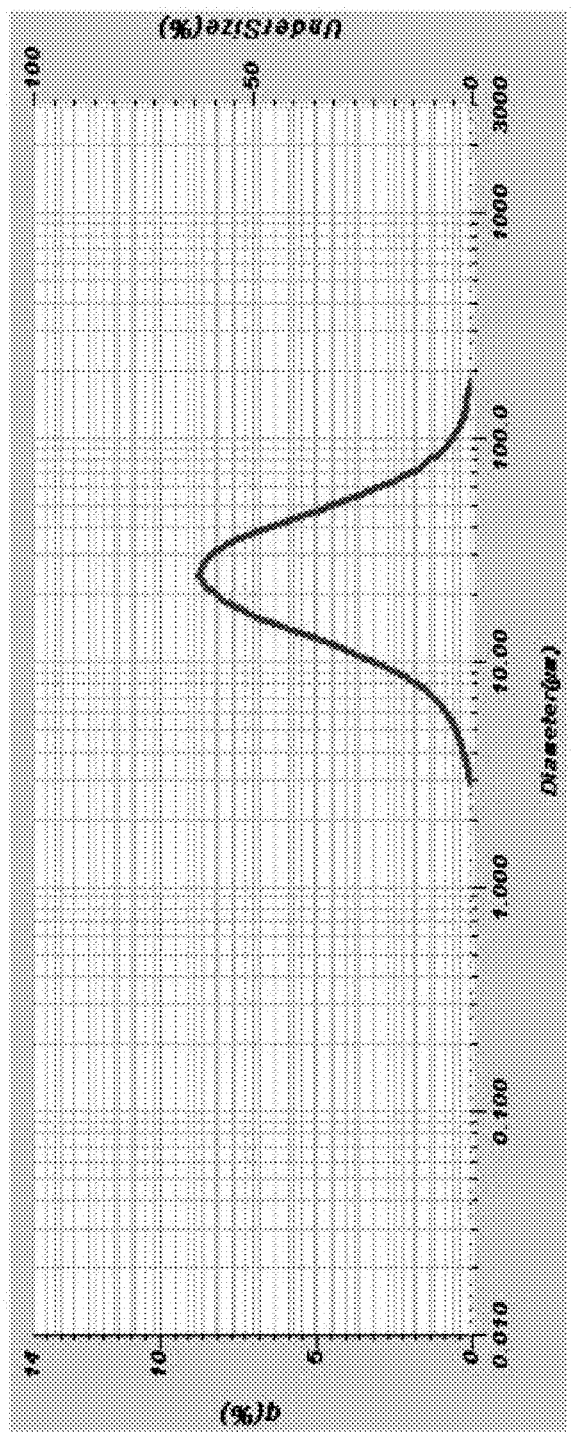
FIG. 2 shows laser scattering particle size distribution analysis of amphetamine in ethyl acetate, 0.5% oleic acid, and cyclohexane.
Figure 3:
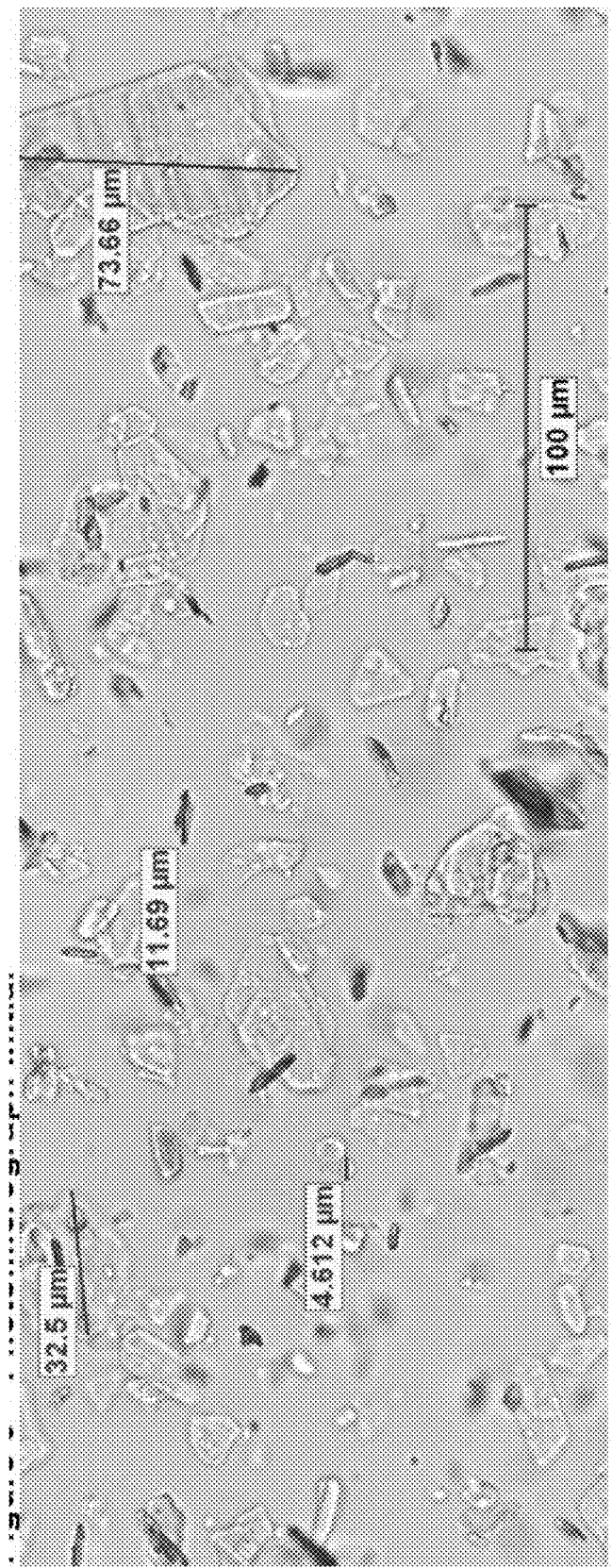
FIG. 3 shows photomicrograph of amphetamine in ethyl acetate, 0.5% oleic acid, and cyclohexane.
Figure 4:
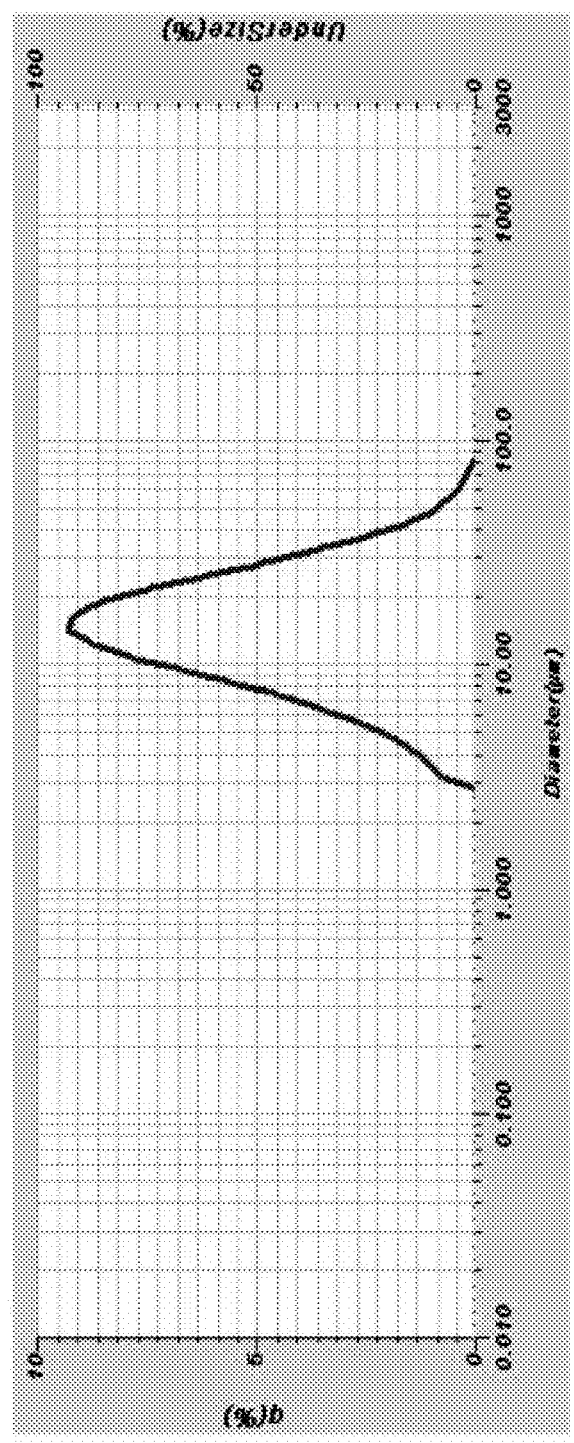
FIG. 4 shows laser scattering particle size distribution analysis of amphetamine 0.5% oleic acid and cyclohexane after 30 minutes of milling.
Figure 5:
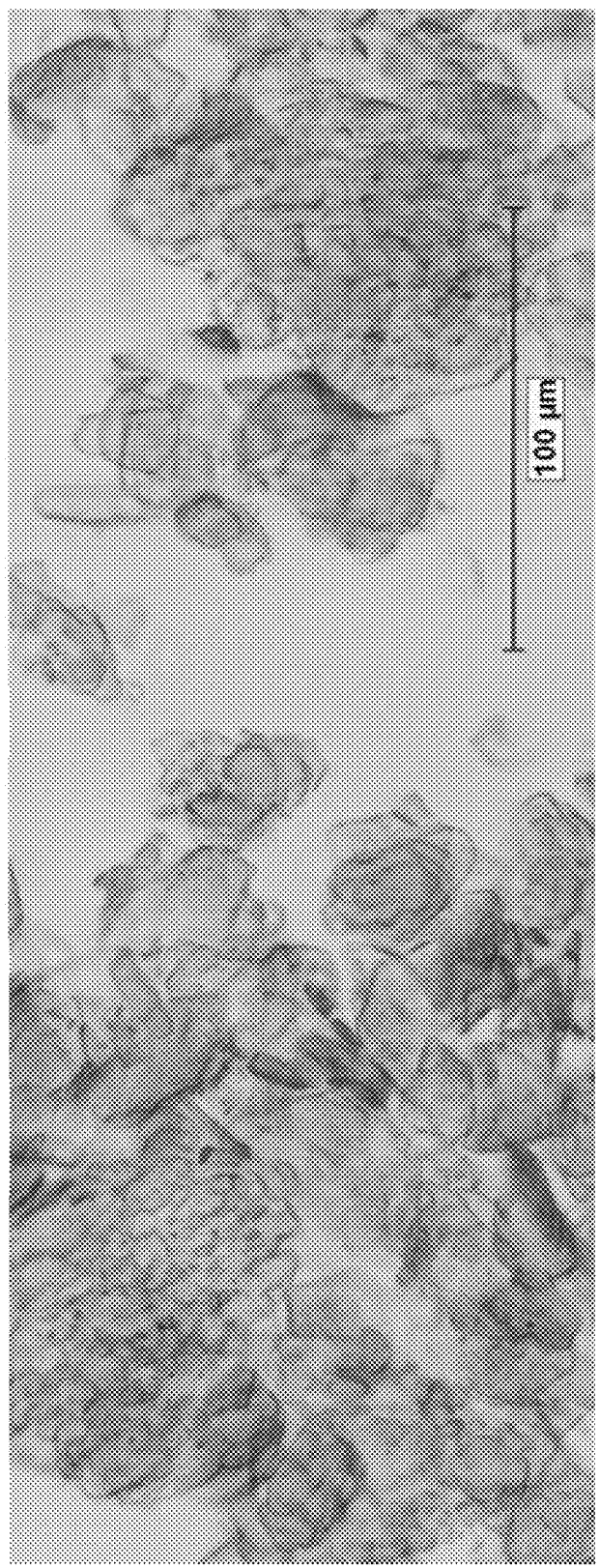
FIG. 5 shows photomicrograph of amphetamine in 0.5% oleic acid and cyclohexane after 30 minutes of milling.
Figure 6:
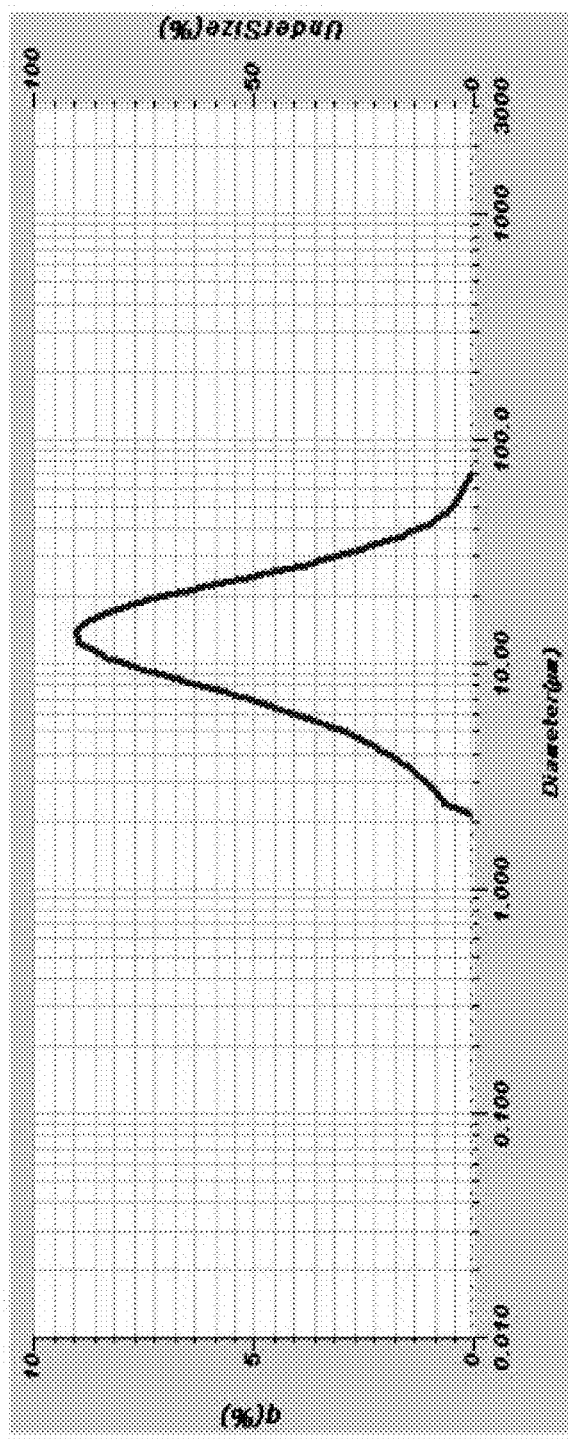
FIG. 6 shows laser scattering particle size distribution analysis of amphetamine 0.5% oleic acid and cyclohexane after 60 minutes of milling.
Figure 7:
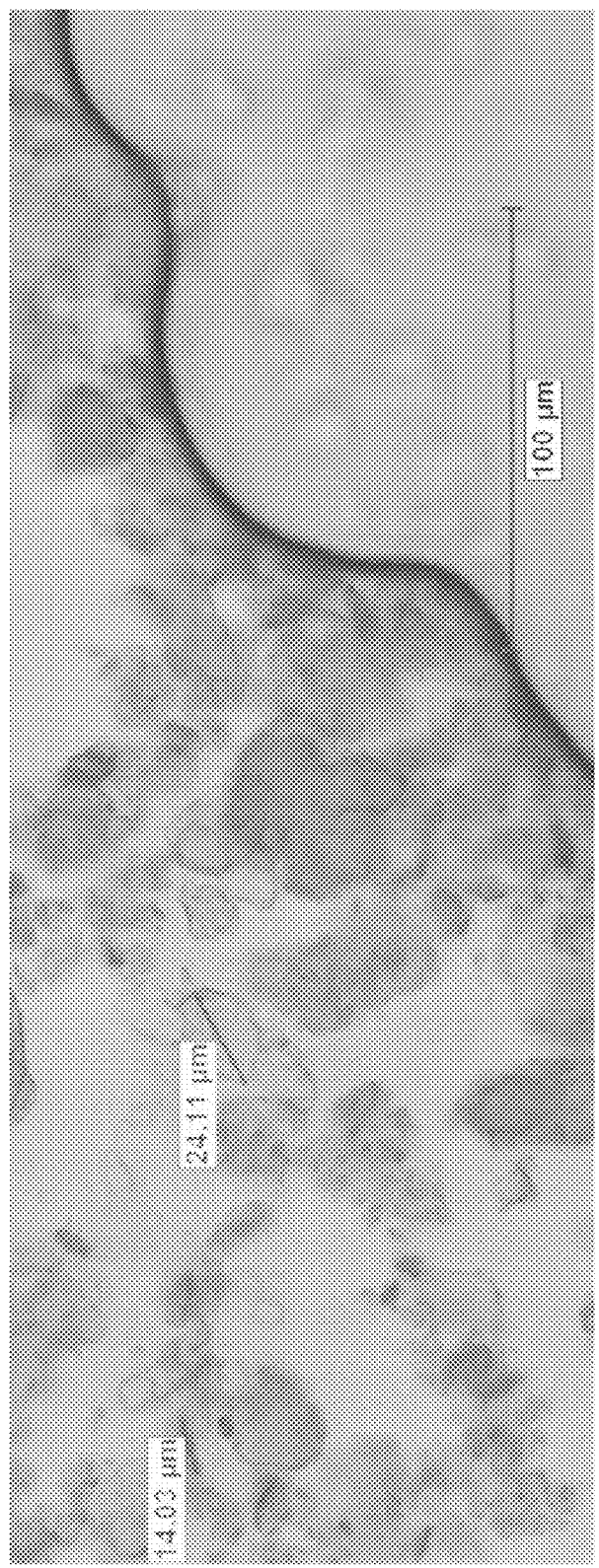
FIG. 7 shows photomicrograph of amphetamine in 0.5% oleic acid and cyclohexane after 60 minutes of milling.
Figure 8:
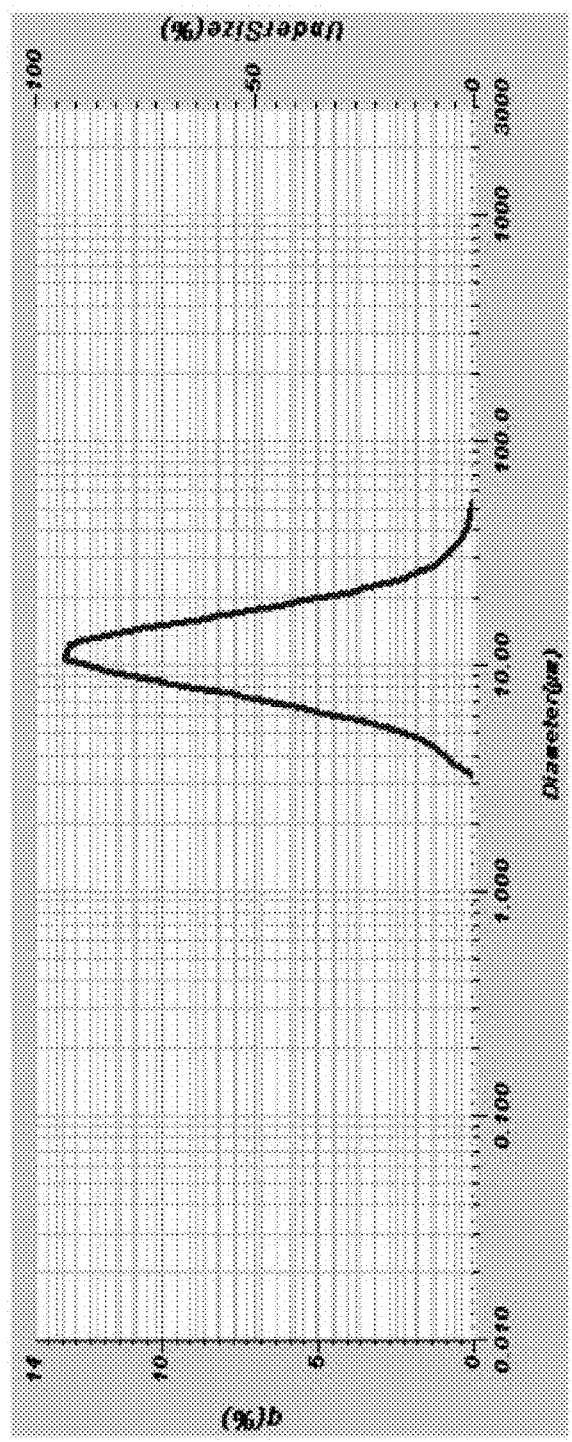
FIG. 8 shows laser scattering particle size distribution analysis of amphetamine 0.5% oleic acid and cyclohexane after 120 minutes of milling.
Figure 9:
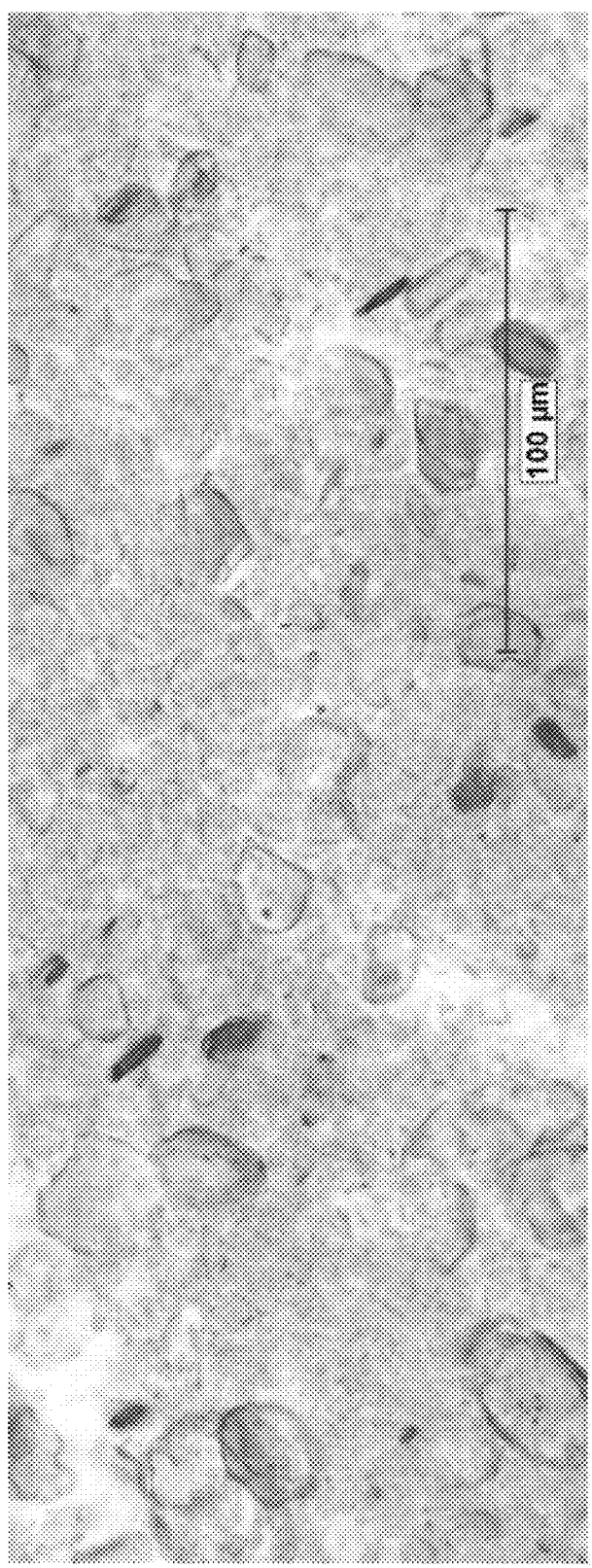
FIG. 9 shows photomicrograph of amphetamine in 0.5% oleic acid and cyclohexane after 120 minutes of milling.
Figure 10:
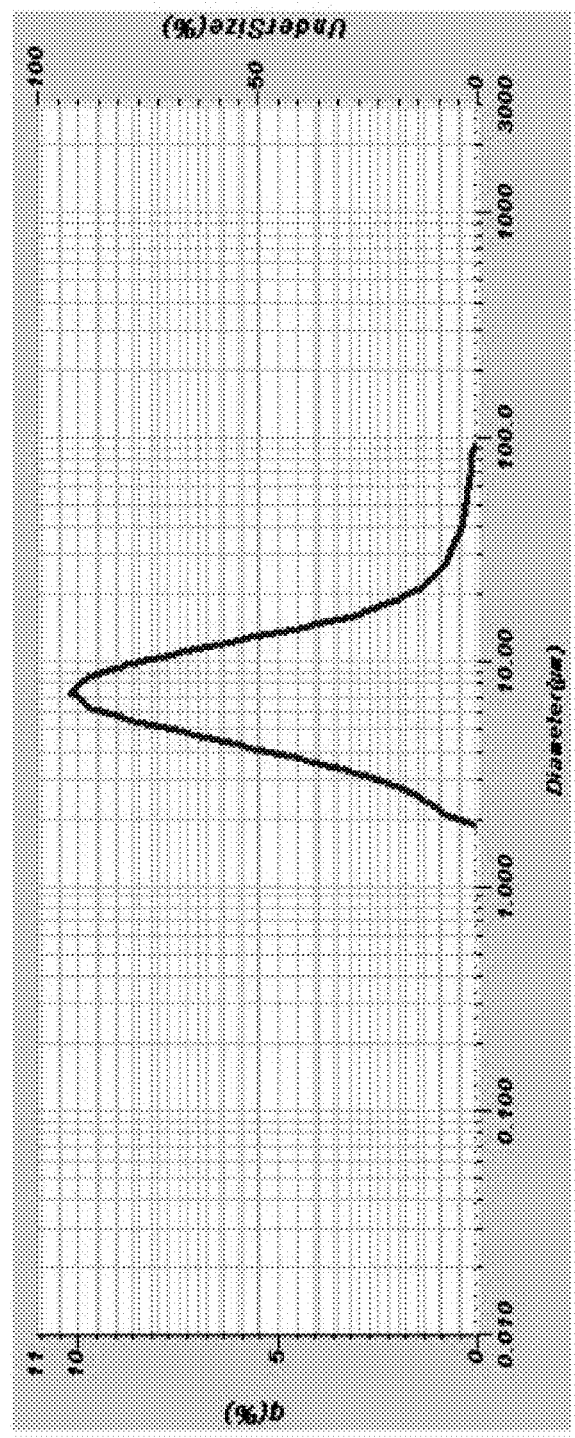
FIG. 10 shows laser scattering particle size distribution analysis of amphetamine 0.5% oleic acid and cyclohexane after 240 minutes of milling.
Figure 11:
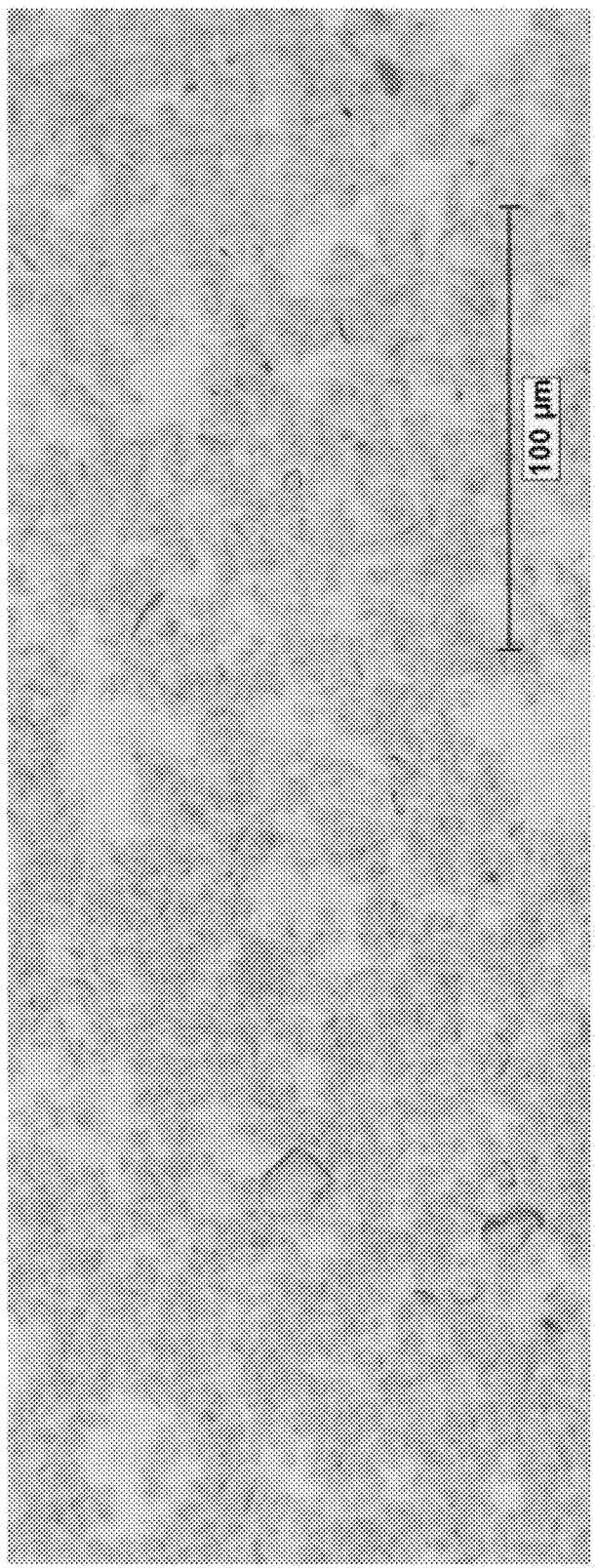
FIG. 11 shows photomicrograph of amphetamine in 0.5% oleic acid and cyclohexane after 240 minutes of milling.

The present invention provides drug therapy formulations (e.g., nanoparticulate formulations, rapid-release formulations, rapid-clearance formulations, delayed release formulations, mixed immediate release and controlled release formulations, etc.). In some embodiments, provided herein are pharmaceutical formulations for reducing the side effects associated with a therapeutic (e.g., stimulant (e.g., Adderall)). In some embodiments, the present invention provides a reduction in sleep- and diet-related side effects associated with a therapeutic (e.g., stimulant (e.g., Adderall)). In some embodiments, the present invention provides drug formulation (e.g. nanoparticulate formulation) for enhanced benefit (e.g., rapid release, rapid clearance, rapid onset of therapeutic effect, reducing the side effects, etc.) of a therapeutic (e.g., stimulant (e.g., Adderall)). In some embodiments, the present invention provides combination drug therapy for prolonging the benefit and/or reducing the side effects of a therapeutic through co-administration with a second therapeutic. In some embodiments, the present invention provides a reduction in sleep- and diet-related side effects associated with a first therapeutic through co-administration with a time-released second therapeutic. In some embodiments, the present invention provides formulations (e.g. nanoparticulate formulation) of one or more therapeutics which allows therapeutic benefit with reduced dosage, thereby reducing side effects (e.g. sleep- and diet-related side effects). In some embodiments, the present invention provides formulations (e.g. nanoparticulate formulation) which provide enhanced bioavailablity, thereby reducing associated side effects (e.g. sleep- and diet-related side effects). In some embodiments, the present invention provides formulations (e.g. nanoparticulate formulation) which provide rapid bioavailablity. In some embodiments, the present invention provides formulations (e.g. nanoparticulate formulation) which provide rapid clearance from the blood (e.g., thereby reducing associated side effects (e.g. sleep- and diet-related side effects)).

In some embodiments, the present invention provides a combination therapy whereby two synergistic pharmacological agents are co-administered to provide prolonged benefit to the patient while reducing side effects associated with one or either individual agent. In some embodiments, co-administration allows reduced dose of one or both agents relative to the amount that would be administered as a single agent therapy. In some embodiments, one or both agents are formulated (e.g. nanoparticle formulation) to provide an additional basis for lowered dosage. In some embodiments, reduced dose of one or both co-administered agents provides a reduction in associated side effects (e.g. insomnia, loss of appetite, abdominal pain, etc.). In some embodiments, one agent is administered as a nanoparticulate to provide rapid bioavailablity and/or rapid clearance of the agent.

In some embodiments, the present invention provides administration of one or more pharmaceutical agents (e.g., stimulant (e.g., Adderall)) in a nanoparticulate formulation. In some embodiments, formulation of the one or more pharmaceutical agents (e.g., stimulant (e.g., Adderall)) in a nanoparticulate provides one or more advantages over non-nanoparticulate formulation (e.g., rapid release, rapid blood clearance, reduced side-effects, lower dosage, enhanced bioavailabilty, etc.). In some embodiments, all the active agents in a pharmaceutical composition are provided in nanoparticulate formulation. In some embodiments, administration as a nanoparticulate allows a similar benefit (e.g. duration of treatment, effectiveness of symptom reduction, etc.) as conventional formulations with reduced dose of the therapeutic agent (e.g., stimulant (e.g., Adderall)). In some embodiments, reducing the dose of the therapeutic agent (e.g., stimulant (e.g., Adderall)) reduces negative side effects (e.g. insomnia, loss of appetite, abdominal pain, etc.) associated therewith (e.g. associated with large doses (e.g. large doses required for prolonging duration of therapeutic benefit). In some embodiments, rapid release of the therapeutic agent (e.g., stimulant (e.g., Adderall)) reduces the associated side effects and/or the required dose. In some embodiments, rapid blood clearance of the therapeutic agent (e.g., stimulant (e.g., Adderall)) reduces the associated side effects.

In some embodiments, one or more pharmaceutical agents are provided in both a nanoparticulate formulation and non-nanoparticulate formulation (e.g., convention formulation, delayed-release formulation, enterically coated, etc.). In some embodiments, providing one or more agents in two different formulations formulations (e.g., nanoparticulate and non-nanoparticulate) provides enhanced bioavailability, reduced side effects, prolonged effect, reduced dosage, etc. In some embodiments, a single pharmaceutical agent (e.g.: a stimulant (e.g., Adderall)) is provided in both a nanoparticulate formulation and non-nanoparticulate formulation (e.g., convention formulation, delayed-release formulation, enterically coated, etc.). In some embodiments, providing a pharmaceutical agent in two different formulations (e.g., nanoparticulate and non-nanoparticulate) provides enhanced bioavailability, reduced side effects, prolonged effect, reduced dosage, etc.

In some embodiments, the present invention provides co-administration of a first agent with a second agent. In some embodiments, one or both agents are formulated as nanoparticulates. In some embodiments, the present invention provides co-administration of a first agent with a time-released second agent. In some embodiments, the first agent is also time released. In some embodiments, the first agent (e.g., stimulant (e.g., Adderall)) is timed to release early in the treatment course (e.g., first agent is in nanoparticulate). In some embodiments, the first agent is formulated (e.g., nanoparticulate) to be cleared from the blood early in the treatment course. In some embodiments, a first agent is formulated with one or more additional pharmaceutical and/or non-pharmaceutical agents. In some embodiments, the second agent is timed to release late in the treatment course. In some embodiments, the second agent is timed to release throughout the treatment course. In some embodiments, administration of the second agent with the first agent allows a similar benefit (e.g. duration of treatment, effectiveness of symptom reduction, etc.) from treatment with reduced dose of the first agent. In some embodiments, reducing the dose of the first agent reduces negative side effects (e.g. insomnia, loss of appetite, abdominal pain, etc.) associated with the first agent (e.g. associated with large doses (e.g. large doses required for prolonging duration of the benefit of the first agent). In some embodiments, rapid release of the first agent reduces the associated side effects and/or the required dose. In some embodiments, rapid blood clearance of the first agent reduces the associated side effects. In some embodiments, administration of the second agent with the first agent allows a similar benefit (e.g. duration of treatment) from treatment with reduced dose of the second agent. In some embodiments, reducing the dose of the second agent reduces negative side effects (e.g. insomnia, loss of appetite, abdominal pain, etc.) associated with the second agent (e.g. associated with large doses (e.g. large doses required for prolonging duration of the benefit of the second agent). In some embodiments, a lower dose of the first agent at an early stage in the treatment course causes the first agent to be substantially metabolized during the later portion of the treatment course such that its active dosage does not exhibit unwanted side effects. In such embodiments, the second agent is active in the later portion of the treatment course to provide or significantly contribute to the therapeutic benefit—without the associated negative effects of the first agent. In some embodiments, nanoparticulate formulation of one or more agents reduces side effects associated with those agents (e.g., due to rapid release and/or rapid clearance of nanoparticulate formulated agents).

In some embodiments a first pharmacologic agent and a second pharmacologic agent provide treatment of the same disorder, disease, condition, and/or symptoms thereof. In some embodiments, first and second agents treat the same disorder, disease, condition, and/or symptoms thereof through different pharmacologic mechanisms. In some embodiments, the differing mechanisms allow for prolonged reduction in symptoms over administration of a single agent. In some embodiments, the differing mechanisms allow for reducing the total dose of one or both pharmacological agents. In some embodiments, the differing mechanisms help reduce side effects associated with one or both agents (e.g. insomnia, abdominal pain, and/or loss of appetite). In some embodiments, reduction in dose of one or both pharmacological agents helps reduce side effects associated with one or both agents.

In some embodiments, the present invention provides co-administration of a first stimulant pharmaceutical with a second non-stimulant pharmaceutical. In some embodiments, one or both of the first stimulant pharmaceutical and second non-stimulant pharmaceutical are nanoparticle formulated. In some embodiments, the present invention provides co-administration of a first stimulant pharmaceutical (e.g. norepinephrine reuptake inhibitor (e.g. amphetamines, methylphenidate, etc.)) with a second non-stimulant pharmaceutical (e.g. alpha adrenergic agonist (e.g. guanfacine, clonidine, etc.) for the treatment of attention deficit hyperactive disorder (ADHD). In some embodiments, a stimulant and non-stimulant are co-administered to provide an extended duration of effective treatment of symptoms without increasing the dose of either agent. In some embodiments, a stimulant and non-stimulant are co-administered to provide an extended duration of effective treatment of symptoms without significant side effects (e.g. insomnia, appetite loss, abdominal pain). In some embodiments, co-administration of a stimulant agent and non-stimulant agent provides extended effective treatment of ADHD (e.g. >8 hours, >10 hours, >12 hours, >14 hours, >16 hours, up to 24 hours) without side effects associated with large doses of stimulants. In some embodiments, co-administration of a stimulant agent and non-stimulant agent provides the same duration of symptom relief as a high dose stimulant-only treatment, using reduced dosage of stimulant and with reduced stimulant side effects (e.g. reduced insomnia, reduced appetite loss, reduced abdominal pain, etc.). In some embodiments, co-administration of a stimulant agent and non-stimulant agent provides extended duration of symptom relief over stimulant-only treatment (e.g. additional 2 hours of reduced symptoms, additional 4 hours of reduced symptoms, additional 6 hours of reduced symptoms, additional 8 hours of reduced symptoms) without additional stimulant side effects (e.g. insomnia, appetite loss, abdominal pain, etc.).

In some embodiments, the present invention provides timed release co-administration of a first stimulant pharmaceutical (e.g. norepinephrine reuptake inhibitor (e.g. amphetamines (e.g., Adderall), methylphenidate, etc.)) with a second non-stimulant pharmaceutical (e.g. alpha adrenergic agonist (e.g. guanfacine, clonidine, etc.)) for the treatment of ADHD. In some embodiments, a first stimulant pharmaceutical is formulated for immediate release, providing a subject with reduced symptoms beginning early in the treatment time course (e.g. within 10 minutes, within 30 minutes, within 1 hour). In some embodiments, a first stimulant pharmaceutical is formulated to last for several hours (e.g. 3 hours, 4 hours, 5 hours, 6 hours, 7 hours, 8 hours). In some embodiments, a first stimulant pharmaceutical is formulated (e.g., in a nanoparticulate) for rapid release and/or clearance (e.g., peak blood concentration in <15 minutes). In some embodiments, a second non-stimulant pharmaceutical is formulated for delayed release, providing a subject with reduced symptoms beginning midway through the treatment time course (e.g. beginning at approximately 3 hours, 4 hours, 5 hours, 6 hours, 7 hours) and lasting for several hours (e.g. 3 hours, 4 hours, 5 hours, 6 hours, 7 hours, 8 hours). In some embodiments, a second non-stimulant pharmaceutical is formulated for slow release, providing a subject with reduced symptoms (e.g. mild reduction in symptoms) beginning early in the treatment time course (e.g. within 10 minutes, within 30 minutes, within 1 hour) and providing a low dosage released over multiple hours (e.g. 8 hours, 9 hours, 10 hours, 11 hours, 12 hours, 13 hours, 14 hours, 15 hours, 16 hours, etc.). In some embodiments, slow-release or delayed-release of the second non-stimulant pharmaceutical agent extends the effective reduction of ADHD symptoms of the first stimulant pharmaceutical agent, without an increase in dose of the stimulant. In some embodiments, slow-release or delayed-release of the second non-stimulant pharmaceutical agent extends the effective reduction of ADHD symptoms of the first stimulant pharmaceutical agent, using a lower dose of the stimulant. In some embodiments, slow-release or delayed-release of the second non-stimulant pharmaceutical agent extends the effective reduction of ADHD symptoms of the first stimulant pharmaceutical agent, without stimulant-related side effects (e.g. without significant stimulant-related side effects.

In some embodiments, the present invention provides combination therapy for the treatment of pediatric ADHD. In some embodiments, the present invention provides timed release co-administration of a first stimulant pharmaceutical (e.g. norepinephrine reuptake inhibitor (e.g. amphetamines, methylphenidate, etc.)) with a second non-stimulant pharmaceutical (e.g. alpha adrenergic agonist (e.g. guanfacine, clonidine, etc.)) for the treatment of pediatric ADHD (e.g. patients under 25, under 22, under 18, under 16, etc.). In some embodiments, child patients present difficulties in compliance with scheduled administration of pharmaceutical treatment. In some embodiments, the school day and/or other childhood-related factors (e.g. desire not to take medicine, desire not to take medicine in front of friends, difficulty remembering to take medicine, etc.) makes administration of a single pharmaceutical dose in the morning the preferred method of treatment for increasing therapy compliance. In some embodiments, traditional stimulant therapies require a large dose of stimulant (e.g. >10 mg, >20 mg, >50 mg, etc.) to provide benefit (e.g. reduced ADHD symptoms, including, but not limited to, ease of distraction, loss of attention to details, forgetfulness, loss of focus, boredom, learning disabilities, difficulty completing projects, problems with listening, daydreaming, confusion, slow movement, difficulties processing information, difficulties following instructions, fidgeting, excessive talking, restlessness, excessive motion, impatience, and outbursts) throughout the desired course (e.g. the entire school day, school day plus afterschool activities, >8 hours, >10 hours, >12 hours, etc.). Large doses of stimulant used in traditional stimulant regimes result in significant side effects such as insomnia, abdominal pain, and loss of appetite that carry over into the later part of the day where they become life disruptive for the subject and those around the subject. Insomnia, abdominal pain, and loss of appetite have significant impact on a child's health and quality of life. In some embodiments, the present invention provides time-released co-administration of a stimulant and non-stimulant in a single dose (e.g. a single dose taken at the beginning of the day or before school). In some embodiments, the present invention provides timed release co-administration of a first stimulant pharmaceutical (e.g. norepinephrine reuptake inhibitor (e.g. amphetamines (e.g., Adderall), methylphenidate, etc.)) with a second non-stimulant pharmaceutical (e.g. alpha adrenergic agonist (e.g. guanfacine, clonidine, etc.)) for full-day treatment of pediatric ADHD (e.g. the entire school day, school day plus afterschool activities, >8 hours, >10 hours, >12 hours, etc.). In some embodiments, co-administration of stimulant and non-stimulant provides extended reduction of symptoms ADHD (e.g. the entire school day, school day plus afterschool activities, >8 hours, >10 hours, >12 hours, etc.) without detrimental side effects (e.g. insomnia, appetite loss, abdominal pain, etc.). In some embodiments, co-administration of stimulant and non-stimulant provides extended reduction of ADHD symptoms without significant detrimental side effects (e.g. insomnia, appetite loss, abdominal pain, etc.). In some embodiments, co-administration of stimulant and non-stimulant provides extended reduction of ADHD symptoms with significantly reduced detrimental side effects (e.g. insomnia, appetite loss, abdominal pain, etc.).

In some embodiments, pharmaceutical agents of the present invention contain additional agents to control side effects (e.g. insomnia, appetite loss, abdominal pain, etc.). In some embodiments, peppermint oil is included with a pharmaceutical agent to reduce abdominal pain associated with one or more pharmaceutical agents (e.g. stimulant agent, non-stimulant agent, etc.). In some embodiments, peppermint oil is included with a pharmaceutical agent to reduce abdominal pain associated with high doses of one or more pharmaceutical agents.

In some embodiments, stimulant pharmaceuticals for use with the present invention include amphetamines (e.g. Adderall XR, Adderall, etc.), lisdexamphetamine (e.g. Vyvanse, etc.), methylphenidate (e.g. Concerta, Ritalin, Ritalin LA, Metadate CD, Metadate ER, etc.), dexmethylphenidate (e.g. Focalin, Focalin XR, etc.), and dexamphetamine (e.g. Dexedrine). Those of skill in the will recognize that this list is not limiting and recognize additional stimulant pharmaceuticals which will find use with embodiments of the present invention. In some embodiments, non-stimulant pharmaceuticals for use with the present invention include Atomoxetine (e.g. Strattera, etc.), Guanfacine (e.g. Intuniv, etc.), Clonidine, etc. Those of skill in the will recognize that this list is not limiting and recognize additional non-stimulant pharmaceuticals which will find use with embodiments of the present invention.

In some embodiments, the present invention provides nanoparticulate formulations of pharmaceutical agents (e.g., a stimulant (e.g., Adderall)) for treatment of ADHD. In some embodiments, embodiments of the present invention (e.g., co-administration, nanoparticulate formulation, etc.) provide enhanced benefit at a standard does, reduced side effects at a standard does (e.g., 10 mg Adderall, 1 mg guanfacine, etc.), standard benefit at a reduced does (e.g., with reduced side effects due to reduced dose), enhanced benefit at a reduced does (e.g., with reduced side effects due to reduced dose), etc. In some embodiments, the present invention provides nanoparticulate formulations of Addreall at doses of less than 100 mg/day (e.g., <50 mg/day, <40 mg/day, <30 mg/day, <20 mg/day, <10 mg/day, <5 mg/day, etc.). In some embodiments, a single dose of Adderall is given each day (e.g., 10 mg, <10 mg). In some embodiments, multiple doses (e.g., 2, 3, 4, 5, 6, or more) of Adderall are given each day. In some embodiments, individual does contain 10 or less mg/does (e.g., 10 mg, 9 mg, 8 mg, 7 mg, 6 mg, 5 mg, 4 mg, 3 mg, 2 mg, 1 mg). In some embodiments, standard benefit (e.g., reduced ADHD symptoms) is achieved with a reduced dose of Adderall (e.g., <40 mg/day, <30 mg/day, <20 mg/day, <10 mg/day, <5 mg/day, etc.). In some embodiments, a single reduced dose (e.g., 9 mg, 8 mg, 7 mg, 6 mg, 5 mg, 4 mg, 3 mg, 2 mg, 1 mg) is given each day.

In some embodiments, nanoparticulate formulation of a therapeutic agent (e.g., stimulant (e.g., Adderall) allows for reduction in stimulant dose by as much as 75% (e.g. >10%, >25%, >50%, etc.) when compared to conventional modes of administration. In some embodiments, nanoparticulate formulation allows for reduced dosage (e.g., 9 mg/dose, 8 mg/dose, 7 mg/dose, 6 mg/dose, 5 mg/dose, 4 mg/dose, 3 mg/dose, 2 mg/dose, 1 mg/dose, or less). In some embodiments, nanoparticulate formulation of a therapeutic agent (e.g., stimulant (e.g., Adderall) provides enhanced bioavailability by as much as 100-fold (e.g. >1.1-fold . . . 1.2-fold . . . 1.5-fold . . . 2-fold . . . 5-fold . . . 10-fold . . . 20-fold . . . 50-fold . . . 100-fold, etc.) when compared to conventional modes of administration. In some embodiments, nanoparticulate formulation speeds the rate at which a pharmaceutical agent (e.g., a stimulant (e.g., Adderall) becomes bioavailable by as much as 100-fold (e.g. >1.1-fold . . . 1.2-fold . . . 1.5-fold . . . 2-fold . . . 5-fold . . . 10-fold . . . 20-fold . . . 50-fold . . . 100-fold, etc.) when compared to conventional modes of administration. In some embodiments, nanoparticulate formulation speeds the rate at which a pharmaceutical agent (e.g., a stimulant (e.g., Adderall) is cleared from the blood by as much as 100-fold (e.g. >1.1-fold . . . 1.2-fold . . . 1.5-fold . . . 2-fold . . . 5-fold . . . 10-fold . . . 20-fold . . . 50-fold . . . 100-fold, etc.) when compared to conventional modes of administration.

In some embodiments, co-administration of stimulant and non-stimulant using formulations of the present invention allows for reduction in stimulant dose by as much as 75% (e.g. >10%, >25%, >50%, etc.) when compared to stimulant-only treatment. In some embodiments, co-administration of stimulant and non-stimulant using formulations of the present invention allows for reduction in stimulant dose by 10-50% (e.g. 10%, 20%, 30%, 40%, 50%) when compared to stimulant-only treatment. In some embodiments, co-administration of stimulant and non-stimulant using formulations of the present invention allows for reduction in non-stimulant dose by as much as 75% (e.g. >10%, >25%, >50%, etc.) when compared to non-stimulant-only treatment. In some embodiments, co-administration of stimulant and non-stimulant using formulations of the present invention allows for reduction in non-stimulant dose by 10-50% (e.g. 10%, 20%, 30%, 40%, 50%) when compared to non-stimulant-only treatment.

In some embodiments, the present invention provides compositions and methods for treatment and/or symptom reduction of attention deficit disorder (ADD), attention deficit hyperactive disorder (ADHD), adult ADD, adult ADHD, pediatric ADD, pediatric ADHD, and related conditions and/or disorders. All embodiments of the invention described herein can be applied to the above conditions and/or disorders. When used for the above purposes, said pharmaceutical compound may be administered via any desired oral, parenateral, topical, intervenous, transmucosal, and/or inhalation routes. The pharmaceutical compound may be administered in the form of a composition which is formulated with a pharmaceutically acceptable carrier and optional excipients, flavors, adjuvants, etc. in accordance with good pharmaceutical practice.

In some embodiments of the present invention, compositions are administered to a patient alone or in combination with other therapies, pharmaceuticals, supplements, and/or a specified diet, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions (e.g. co-administrations of stimulant and non-stimulant) may be administered alone to individuals suffering from ADHD.

Depending on the goal of administration (e.g. severity of condition, duration of treatment, etc.), compositions (e.g. co-administrations of stimulant and non-stimulant) may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

In some embodiments, compositions (e.g. nanoparticulat drg formulations, co-administrations of stimulant and non-stimulant, etc.) are in the form of a solid, semi-solid or liquid dosage form: such as tablet, capsule, orally-disintegrating tablets, pill, powder, suppository, solution, elixir, syrup, suspension, cream, lozenge, paste and spray containing the first and second agents formulated appropriately to provide the desired time-release profile. As those skilled in the art would recognize, depending on the chosen route of administration, the composition form is selected.

In some embodiments, the pharmaceutical composition (e.g., nanoparticulate, multiple co-administered compounds, etc.) are administered in single or multiple doses. In preferred embodiments, the pharmaceutical compound is administered in a single dose. In some embodiments, a single oral pill or capsule is provided containing the first and second agents. In some preferred embodiments, a capsule is used containing the first agent in a form that permits early release and the second agent in a form that permits later release. The particular route of administration and the dosage regimen will be determined by one of skill, in keeping with the condition of the individual to be treated and said individual's response to the treatment. In some embodiments, a single oral pill or capsule is provided containing a nanoparticulate formulation of one or more therapeutic agents (e.g., a stimulant (e.g., Adderall).

In some embodiments, substituents of a composition of the present invention may be adjusted to provide desirable solubility or other characteristics for administration by any suitable technique.

In some embodiments, pharmaceutical agents of the present invention are formulated for slow release, delayed release, immediate release, timed release, or combinations thereof. In some embodiments, a pharmaceutical agent, or portions of a pharmaceutical agent, is enterically coated to protect the agent or agents from dissolving in the stomach. In some embodiments, enterically coated pharmaceuticals dissolve, releasing pharmaceutical agents, upon reaching a desired location (e.g., the small intestine). In some embodiments, enteric coating of an agent delays release of the agent for several hours (e.g. 3 hours, 4 hour, 5 hours, 6 hours, 7 hours, etc.). In some embodiments, an enterically coated agent may be formulated for immediate release upon loss of the enteric coating or for slow release (e.g. over the course of hours). In some embodiments, an enterically coated agent may be formulated for immediate release upon loss of the enteric coating.

The present invention also provides pharmaceutical compositions in a unit dosage form for administration to a subject, comprising pharmaceutical compounds (e.g. stimulant and non-stimulant) and one or more nontoxic pharmaceutically acceptable carriers, adjuvants or vehicles. The amount of the active ingredients (e.g. stimulant and non-stimulant) that may be combined with such materials to produce a single dosage form will vary depending upon various factors, as indicated above. A variety of materials can be used as carriers, adjuvants, and vehicles in the composition of the invention, as available in the pharmaceutical art.

In some embodiments, the present invention provides nanoparticulate formulations of one or more pharmacologic agents. In some embodiments, a single pharmacologic agent is provided in a nanoparticulate formulation. In some embodiments, the present invention provides nanoparticulate formulations comprising one or more pharmacologic agents (e.g., a stimulant (e.g., Adderall)) for the treatment of ADHD. In some embodiments, the present invention provides nanoparticulate formulations comprising one or more stimulant pharmacologic agents. In some embodiments, the present invention provides nanoparticulate formulations comprising one or more non-stimulant pharmacologic agents. In some embodiments, the present invention provides nanoparticulate formulations comprising one or more stimulant pharmacologic agents and one or more non-stimulant pharmacologic agents. In some embodiments, methods of making nanoparticulate formulations comprising pharmacologic agents, and uses and methods of administration thereof are understood in the art (See, e.g., U.S. Pat. Nos. 5,145,648; 5,641,515; 6,592,903; 5,585,108; 5,518,738; 6,375,986; 7,198,795; 5,518,187; 5,862,999; 5,718,388; 5,510,118; herein incorporated by reference in their entireties). In some embodiments, nanoparticulate formulation provides pharmaceutical compositions with enhanced bioavailability. In some embodiments, nanoparticulate formulation provides pharmaceutical compositions with desirable release characteristics (e.g. controlled release, delayed release, slow release, etc.). In some embodiments, nanoparticulate formulation provides pharmaceutical compositions with rapid bioavailability (e.g., <1 hour, <30 minutes, <15 minutes, <5 minutes, <1 minute, <30 seconds, <10 seconds, etc.). In some embodiments, nanoparticulate formulation provides pharmaceutical compositions with rapid blood clearance, for example, the majority of the pharmaceutical composition is cleared from the blood within 1 hour (e.g., <1 hour, <30 minutes, <15 minutes, <5 minutes, <1 minute, <30 seconds, <10 seconds, etc.). In some embodiments, nanoparticulate formulation of pharmacologic agents provides enhanced therapeutic benefit. In some embodiments, reduced dosage of a nanoparticulate formulation of one or more pharmacologic agents provides similar therapeutic benefit to conventional formulations at conventional dosages. In some embodiments, nanoparticulate formulation of one or more pharmacologic agents provides reduced side effects (e.g., insomnia, appetite loss, abdominal pain, etc.). In some embodiments, nanoparticulate formulation of one or more pharmacologic agents provides reduced side effects (e.g. insomnia, appetite loss, abdominal pain, etc.) because lower doses are used to achieve the same benefit as conventional formulations. In some embodiments, nanoparticulate formulation of one or more pharmacologic agents provides reduced side effects (e.g. insomnia, appetite loss, abdominal pain, etc.) because of the rapidity of bioavailability compared to conventional formulations. In some embodiments, nanoparticulate formulation of one or more pharmacologic agents provides reduced side effects (e.g. insomnia, appetite loss, abdominal pain, etc.) because of the rapidity of blood clearance compared to conventional formulations. In some embodiments, nanoparticulate formulation of one or more pharmacologic agents provides reduced side effects (e.g. insomnia, appetite loss, abdominal pain, etc.) because the controlled release properties of nanoparticulate formulation provide more optimal levels of pharmacologic agents circulating in the bloodstream of a subject, although the present invention is not limited to any particular mechanism of action and an understanding of the mechanism of action is not necessary to practice the present invention. In some embodiments, nanoparticulate formulation of stimulant and/or non-stimulant allows for reduction in dose or stimulant and/or non-stimulant by as much as 75% (e.g. >10%, >25%, >50%, etc.) when compared to conventional treatment. In some embodiments, nanoparticulate formulation of stimulant and/or non-stimulant allows allows for reduction in stimulant dose by 10-50% (e.g. 10%, 20%, 30%, 40%, 50%) when compared to conventional treatment.

In some embodiments, pharmaceutical nanoparticulates (e.g., containing Adderall) have a diameter (e.g., mean diameter) of less than about 10 µm (e.g., <10 µm, <5 µm, <2 µm, <1 µm, <500 nm, <200 nm, <100 nm, <50 nm, <20 nm, <10 nm, etc.). In some embodiments, pharmaceutical nanoparticulates (e.g., containing Adderall) have a diameter (e.g., mean diameter) of about 450-550 nm (e.g., about 500 nm). In some embodiments, pharmaceutical nanoparticulates (e.g., containing Adderall) have a diameter (e.g., mean diameter) of about 350-450 nm (e.g., about 400 nm). In some embodiments, pharmaceutical nanoparticulates (e.g., containing Adderall) have a diameter (e.g., mean diameter) of about 250-350 nm (e.g., about 300 nm). In some embodiments, pharmaceutical nanoparticulates (e.g., containing Adderall) have a diameter (e.g., mean diameter) of about 150-250 nm (e.g., about 200 nm). In some embodiments, pharmaceutical nanoparticulates (e.g., containing Adderall) have a diameter (e.g., mean diameter) of about 50-150 nm (e.g., about 100 nm). In some embodiments, pharmaceutical nanoparticulates (e.g., containing Adderall) have a diameter (e.g., mean diameter) of about 25-75 nm (e.g., about 50 nm).
Experimental Example 1

Pediatric ADHD Co-Administration Regimen

Patient dosing is determined on an individual patient basis taking into account the age, size, and weight of the patient; severity of the condition; and empirical response to the treatment. Exemplary stimulant and non-stimulant dose and time-release regimens within the scope of the present invention are provided below. One of skill in the art would understand that the co-administration therapy can be altered, for general practice or for specific patients, in terms of dose, timing of release, and rate of release for either agent.

Exemplary Regimen A.

Patient is administered 10 mg of amphetamine salts (e.g. Dexamphetamine) and 1 mg guanfacine in a single dose in the early part of the day (e.g. morning). The amphetamine salts are formulated for immediate release, and the guanfacine is formulated for delayed release. Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course (e.g. morning), and the guanfacine extends the reduction of symptoms throughout the later portion of the time course (e.g. afternoon); therefore, the combination reduces symptoms over the entire time-course with reduced side effects caused by multiple doses.

Exemplary Regimen B.

Patient is administered 9 mg of amphetamine salts (e.g. Dexamphetamine) and 0.9 mg guanfacine (10% reduction in total daily dose) in a single dose in the early part of the day (e.g. morning). The amphetamine salts are formulated for immediate release over approximately 5 hours, and the guanfacine is formulated for release beginning after a 4 hours and continuing for approximately 5 hours. Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course (e.g. morning), and the guanfacine extends the reduction of symptoms throughout the later portion of the time course (e.g. afternoon).

EXEMPLARY REGIMEN C.

Patient is administered 9 mg of amphetamine salts (e.g. Dexamphetamine) and 0.9 mg guanfacine (10% reduction in total daily dose) in a single dose in the early part of the day (e.g. morning). The amphetamine salts are formulated for release by two separate mechanisms. 5 mg are formulated for immediate release. 4 mg are coated for enteric release (e.g. release after approximately 4 hours). The guanfacine is formulated for release beginning after 4 hours and continuing for approximately 5 hours. Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course, which is supplemented by the enteric release several hours later. The guanfacine extends the reduction of symptoms throughout the later portion of the time course (e.g. afternoon) without undesired side effects.

Exemplary Regimen D.

Patient is administered 9 mg of amphetamine salts (e.g. Dexamphetamine) and 0.9 mg guanfacine (10% reduction in total daily dose) in a single dose in the early part of the day (e.g. morning). The amphetamine salts are formulated for release by two separate mechanisms. 5 mg are formulated for immediate release. 4 mg are coated for enteric release (e.g. release after approximately 4 hours). The guanfacine is coated for enteric release beginning after approximately 4 hours and formulated for slow release continuing over the course of several hours (e.g. 4 hours, 5 hours, 6 hours, 7 hours, 8 hours, 9 hours, 10 hours, etc.). Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course, which is supplemented by the enteric release several hours later. The guanfacine extends the reduction of symptoms throughout the late portion of the time course without undesired side effects.

In any of the above regimens, peppermint oil may be included in the formulation, either as immediate release, or, for example, may be enterically coated (e.g., alone with other components) for immediate release after several hours to target both the timing and location of abdominal pain side effects associated with some therapeutic agents.

Example 2

Nanoparticulate Formulation Dosing

Exemplary stimulant and/or non-stimulant dose and time-release regimens, for use with nanoparticulate formulation, within the scope of the present invention is provided below. One of skill in the art would understand that the regimens can be altered, for general practice or for specific patients, in terms of dose, formulation, combinations, timing of release, and rate of release for one or more agents.

Exemplary Regimen A.

Patient is administered 10 mg of a nanoparticulate formulation of amphetamine salts (e.g. Dexamphetamine) in a single dose in the early part of the day (e.g. morning). The amphetamine salts are formulated for immediate release over approximately 5 hours. Although the present invention is not limited to any particular mechanism of action and an understanding of the mechanism of action is not necessary to practice the present invention, it is contemplated that in this configuration the nanoparticulate formulation provides enhanced bioavailability of Dexamphetamine, thereby allowing a reduced dose, resulting in reduce side effects.

Exemplary Regimen B.

Patient is administered 6 mg of a nanoparticulate formulation of amphetamine salts (e.g. Dexamphetamine) and 0.9 mg guanfacine (10% reduction in total daily dose) in a single dose in the early part of the day (e.g. morning). The amphetamine salts are formulated for immediate release over approximately 5 hours, and the guanfacine is formulated for release beginning after a 4 hours and continuing for approximately 5 hours. Although the present invention is not limited to any particular mechanism of action and an understanding of the mechanism of action is not necessary to practice the present invention, it is contemplated that in this configuration the nanoparticulate formulation of Dexamphetamine provides a rapid reduction in symptoms, at a reduced dosage, continuing through the early hours of the time-course (e.g. morning), and the guanfacine extends the reduction of symptoms throughout the later portion of the time course (e.g. afternoon).

Exemplary Regimen C.

Patient is administered 9 mg of a nanoparticulate formulation of amphetamine salts (e.g. Dexamphetamine) in a single dose in the early part of the day (e.g. morning). The nanoparticulate amphetamine salts are formulated for release by two separate mechanisms. 5 mg are formulated for immediate release. 4 mg are coated for enteric release (e.g. release after approximately 4 hours). The guanfacine is formulated for release beginning after 4 hours and continuing for approximately 5 hours. Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course, which is supplemented by the enteric release several hours later. It is contemplated that in this configuration the nanoparticulate formulation provides enhanced bioavailability of Dexamphetamine, thereby allowing a reduced dose, resulting in reduce side effects.

Exemplary Regimen D.

Patient is administered 6 mg of a nanoparticulate formulation of amphetamine salts amphetamine salts (e.g. Dexamphetamine) and 0.6 mg a nanoparticulate formulation of guanfacine in a single dose in the early part of the day (e.g. morning). The nanoparticulate amphetamine salts are formulated for release by two separate mechanisms. 3.5 mg are formulated for immediate release. 2.5 mg are coated for enteric release (e.g. release after approximately 4 hours). The nanoparticulate guanfacine is formulated for release beginning after 4 hours and continuing for approximately 5 hours. Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course, which is supplemented by the enteric release several hours later. The guanfacine extends the reduction of symptoms throughout the later portion of the time course (e.g. afternoon) without undesired side effects. It is contemplated that in this configuration the nanoparticulate formulation provides enhanced bioavailability, thereby allowing a reduced dose, resulting in reduce side effects.

Exemplary Regimen E.

Patient is administered 7 mg of a nanoparticulate formulation of amphetamine salts (e.g. Dexamphetamine) and 0.7 mg of a nanoparticulate formulation of guanfacine (10% reduction in total daily dose) in a single dose in the early part of the day (e.g. morning). The nanoparticulate amphetamine salts are formulated for release by two separate mechanisms. 4 mg are formulated for immediate release. 3 mg are coated for enteric release (e.g. release after approximately 4 hours). The guanfacine is coated for enteric release beginning after approximately 4 hours and formulated for slow release continuing over the course of several hours (e.g. 4 hours, 5 hours, 6 hours, 7 hours, 8 hours, 9 hours, 10 hours, etc.). Although the present invention is not limited to any particular mechanism of action and an understanding of the mechanism of action is not necessary to practice the present invention, it is contemplated that in this configuration the Dexamphetamine provides a rapid reduction in symptoms continuing through the early hours of the time-course, which is supplemented by the enteric release several hours later. The guanfacine extends the reduction of symptoms throughout the late portion of the time course without undesired side effects. It is contemplated that in this configuration the nanoparticulate formulation provides enhanced bioavailability, thereby allowing a reduced dose, resulting in reduce side effects.

In any of the above regimens, peppermint oil may be included in the formulation, either as immediate release, or, for example, may be enterically coated (e.g., alone with other components) for immediate release after several hours to target both the timing and location of abdominal pain side effects associated with some therapeutic agents.

Example 3

Deterrent of Abuse

Stimulants, such as amphetamines and methylphenidate, are widely abused as prescription products. The stimulants elevate the levels of dopamine as well as nor-epinephrine. Non-stimulants on the other hand act only by increasing the levels of nor-epinephrine. Drugs that elevate dopamine (e.g. amphetamine, methamphetamine, cocaine) make people euphoric. Due to this pharmacologic effect, stimulant drugs are abused whereas non-stimulant drugs typically are not. According to the National Institutes on Drug Abuse (part of the NIH) stimulants are abused for both "performance enhancement" and recreational purposes. For the former, they suppress appetite and facilitate weight loss. The euphoric effects of stimulants usually occur when they are crushed and then snorted or injected. Some abusers dissolve the tablets in water and inject the mixture.

In some embodiments, the present invention provides compositions, systems, and methods to deter the abuse of stimulant drugs in the treatment of ADHD. In some embodiments, the present invention provides compositions and methods to deter subjects from taking unadvisable, off-prescription, and/or unintended dosages of pharmaceuticals of the present invention. In some embodiments, the present invention provides compositions and methods to deter subjects from taking and/or administering pharmaceuticals of the present invention via unintended, off-prescription, and/ or unadvisable routes (e.g. intravenously, snorting, etc.). In some embodiments, the present invention includes an abuse deterrent formulation for reducing the potential for one or more of a) parenteral abuse, b) inhalation (e.g., intranasal abuse), and/or c) oral abuse of a drug, for satisfaction of a physical or psychological dependence. In some embodiments, the invention comprises combining stimulant and non-stimulant drugs in a once daily dosing regimen, where the stimulant dose is reduced (e.g. reduced by 10-50%). In some embodiments, the invention provides stimulant and non-stimulant drugs in a tamper resistant formulation wherein the stimulant is combined with a polymer (e.g. polyethylene oxide, polyvinyl alcohol, hydroxypropyl methyl cellulose, carbomers, other such pharmaceutical agents, etc.) or suitable pharmaceutical excipients to form a matrix that will make it difficult for a person to abuse by dissolving the dosage form in water or solvent and or snorting or injecting the solution. In some embodiments, the invention provides stimulant and non-stimulant drugs combined with an irritant. In some embodiments, reduction of stimulant dose, combination with an irritant, a formulation that is difficult to tamper with, or a combination thereof provides a deterrent to abuse of compositions of the present invention.

In some embodiments, a pharmaceutical composition of the present invention comprises a surfactant present in sufficient amount to cause nasal irritation. In some embodiments, a pharmaceutical composition of the present invention comprises an inert excipient in sufficient amount to cause emesis if greater than a prescribed amount included in the therapeutic composition is ingested. In some embodiments, a pharmaceutical composition of the present invention comprises an emetic in sufficient amount to cause emesis if greater than a prescribed amount of the analgesic included in the therapeutic composition is ingested. In some embodiments, the amount of emetic present in a pharmaceutical composition of the present invention can be tied directly to the amount of drug in the pharmaceutical composition. Thus, by controlling the quantity of the emetic compound in the pharmaceutical composition, emesis can be avoided if normal prescription directions are followed. However, if an overdosage occurs by ingesting more than a prescribed quantity of a drug in a pharmaceutical composition of the present invention, the amount of ingested emetic can exceed the threshold amount necessary to induce emesis.

In some embodiments, the present invention deters inhalation abuse by providing a pharmaceutical composition which includes one or more mucous membrane, mucosa or mucosal tissue irritants (collectively referred to as mucous membrane irritants). In one embodiment, suitable mucous membrane irritants and/or nasal passageway tissue irritants include compounds that are generally considered pharmaceutically inert, yet can induce irritation. Such compounds include, but are not limited to surfactants. In some embodiments, suitable surfactants include sodium lauryl sulfate, poloxamer, sorbitan monoesters, glyceryl monooleates, etc. Other suitable compounds are believed to be within the knowledge of a practitioner skilled in the relevant art, and can be found in the Handbook of Pharmaceutical Excipients, 4th Ed. (2003), the entire content of which is hereby incorporated by reference. In some embodiments, two or more of the abuse deterrents can be combined into one composition according to the present invention.

In some embodiments, the present invention incorporates or applies abuse deterrent compositions, dosages, and methods known in the art (U.S. Pat. Nos. 7,510,726; 7,476,402; herein incorporated by reference in their entireties). In some embodiments, the abuse deterrent compositions and methods described herein find use with any embodiments of the present invention.

Example 4

Nanoparticulate Formulation

In some embodiments, experiments were performed during development of embodiments of the present invention to produce nanoparticles comprising pharmaceutical compositions (e.g., mixture of amphetamines) with a reduced particle size distribution. Experiments were conducted to decrease the particle size of an amphetamine mixture to a median size below 400 nm. A milling procedure, in which active pharmaceutical ingredients (APIs), were milled together to produce nanoparticles, was used. Successfully milled API was be loaded into hard gelatin capsules for use in a non-GLP in vivo study to compare pharmacokinetics to the commercially available dosage form. The amphetamine milled was a 3:1 D:L mixture of amphetamine isomers, obtained by preparing a 1:1 mixture of amphetamine and the racemic mixture dextroamphetamine. The sulfate salt of each API was used for the project sourced from Johnson-Matthey Plc.

The inherent water solubility of the two amphetamine salts necessitated milling in non-aqueous vehicles. Vehicles were identified that exhibited: 1) minimal solvency for the APIs, and 2) sufficient volatility to allow for their removal to yield a dry powder of the milled material. Based on these criteria: ethyl acetate, methylene chloride, hexanes, and cyclomethicone were identified as potential milling vehicles.

The initial particle size distribution of the mixture was measured using a Horiba LA-950V2 with a median size of approximately 32 µm (SEE FIG. 1). Suspensions at 5% of the 1:1 mixture of amphetamine salts in each of the identified vehicles were made, and roller milled in 20 mL glass vials using 0.5 mm YTZ milling media. The vials were rolled on a US Stoneware laboratory roller mill with particle size measured after four and 16 hours of milling. No additives or dispersants were used in these initial trials so as not to complicate drying and recovery as to calculation of yield.

Microscopic analysis revealed that the milling procedure resulted in a size reduction in all milling vehicles, though this was not indicated in the PSD measurements using the Horiba due to agglomeration of the milled particles. Additional measurements were made adding 0.1% oleic acid as a dispersant to the cyclohexane used as diluent for the measurement, resulting smaller sizes, though still not representative to that seen microscopically (See Table 1).

TABLE 1

Roller Milling Results

| | Median Particle Size [µ] Roller Milling | | | | |
| --- | --- | --- | --- | --- | --- |
| | PSD in Cyclohexane | | PSD 0.1% Oleic acid in Cyclohexane | | |
| Solvent | 4 hr | 16 hr | 16 hr | 24 hr | 24 hr w/ 30 min sonic |
| Ethyl Acetate | 21.3 | 26.4 | 8.7 | 21.1 | 10.4 (300 nm) |
| Methylene Chloride | 33.7 | 45.9 | 12.8 | 23.6 | 8.7 |
| Hexane | 13.5 | No signal | No signal | 4.1 | N/A |
| Cyclomethicone | 31.9 | 17.4 | 8.2 (300 nm) | 10.9 | 18.1 |

Sonication was applied to the preparations which reduced size further, though not be representative of actual primary particle size observed microscopically.

Hexanes presented a particular issue in that the API particles appeared to fuse/heavily agglomerate to the media resulting in a lack of measurable particles, and further work was discontinued using this vehicle. Some samples did exhibit evidence of a bimodal distribution with a population at the target range (values in parenthesis in Table 1).

To speed the rate of milling, the ethyl acetate and methylene chloride samples were transferred to spindle milling. In spindle milling, the media is stirred rather than depending on gravity to move the media as in roller milling, allowing input of a higher level of energy to the grinding. Some additional particle size reduction was found after two hours of spindle milling, though still not judged representative of that observed microscopically. In effort to disperse the observed agglomerates, a higher level of 0.5% oleic acid was tried for the PSD preparation diluent, but did not provide appreciably better results (See Table 2). Graying of the samples was also observed likely due to abrasion of the stainless steel spindle, so this approach was not pursued further.

TABLE 2

Spindle Milling Results

| | Median Particle Size [μ] Spindle Milling | | |
|---|---|---|---|
| | PSD 0.1% Oleic acid in Cyclohexane | | PSD 0.5% Oleic acid in Cyclohexane |
| Solvent | 2 hr | 2 hr w/ 5 min sonication | 2 hr w/ 5 min sonication |
| Ethyl Acetate | 10.4 | 11.1 | 8.9 |
| Methylene Chloride | 17.6 | 11.6 | 10.5 |

To determine if the cause of agglomeration was caused by overgrinding, an investigation was started to determine particle size versus milling time. Roller milling in ethyl acetate with no milling aid or dispersant was used, with particle size measured at initial and 30, 60, 120, and 240 minutes. From these results, the progression of particle size reduction was as desired and evidence of overgrinding was not observed (SEE FIGS. 2-11).

Figure 12:
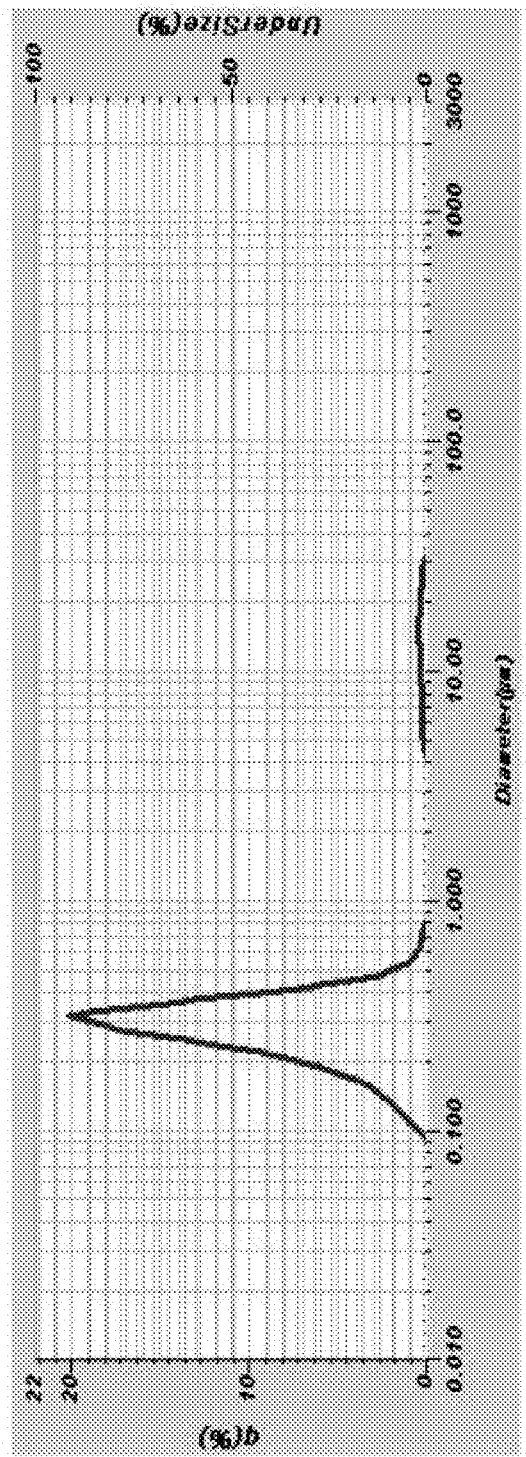
FIG. 12 shows laser scattering particle size distribution analysis of amphetamine 0.5% Sedefos 75 and cyclohexane after 240 minutes of milling.
Figure 13:
FIG. 13 shows photomicrograph of amphetamine in Sedefos 75 and cyclohexane after 240 minutes of milling.
Figure 14:
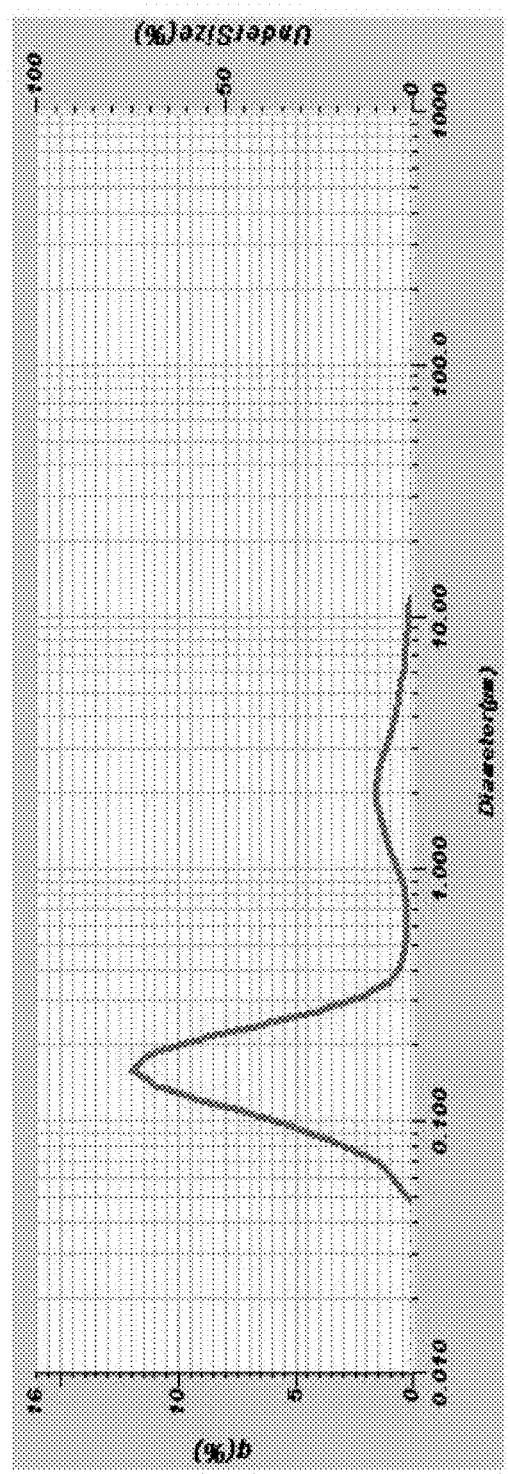
FIG. 14 shows laser scattering particle size distribution analysis of amphetamine in ethanol after 40 hours of milling.
Figure 15:
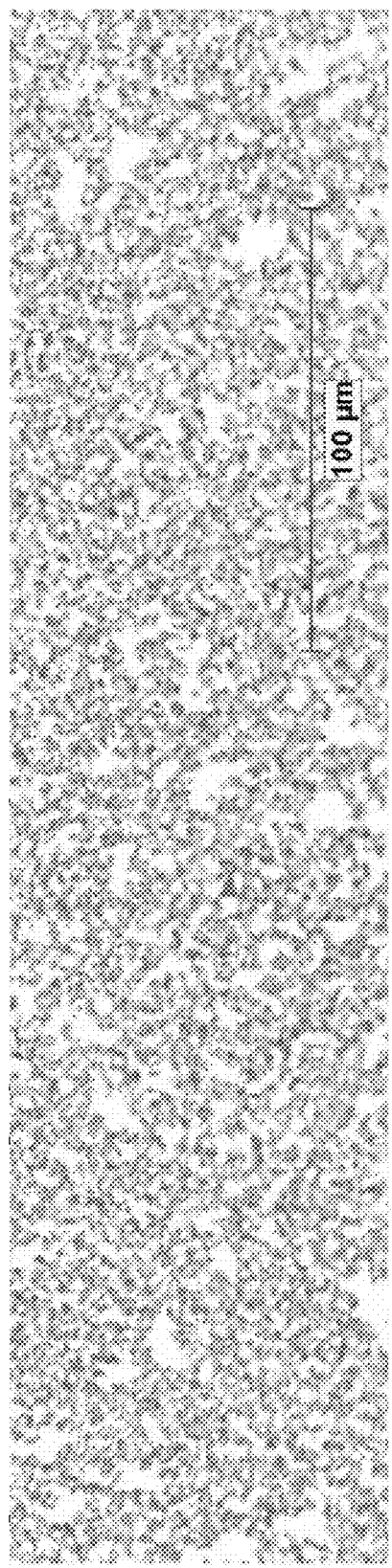
FIG. 15 shows photomicrograph of amphetamine in Sedefos 75 and cyclohexane after 40 hours of milling.

Experiments conducted during development of embodiments of the present invention indicated that APIs were milling well, but could not be dispersed well enough to accurately measure the primary particle size. Alternate dispersants were investigated to overcome this difficulty. Sedefos75 (Gattefosse) was identified to provide good dispersion of the milled APIs for particle size measurement (SEE FIGS. 12 and 13). However, the Sedefos was also found to form micelles in ethyl acetate of similar size, especially in the presence of trace water in the ethyl acetate, leading to uncertainty of the accuracy of the measurement. During investigations, anhydrous ethanol was found to disperse the APIs well without the addition of any dispersant, and a milling trial was performed giving a median size of 200 nm after 40 hr of milling, measured without the addition of any dispersant (SEE FIGS. 14 and 15). The milling was performed at a loading of 5% of the amphetamine mixture in the ethanol.

Figure 16:
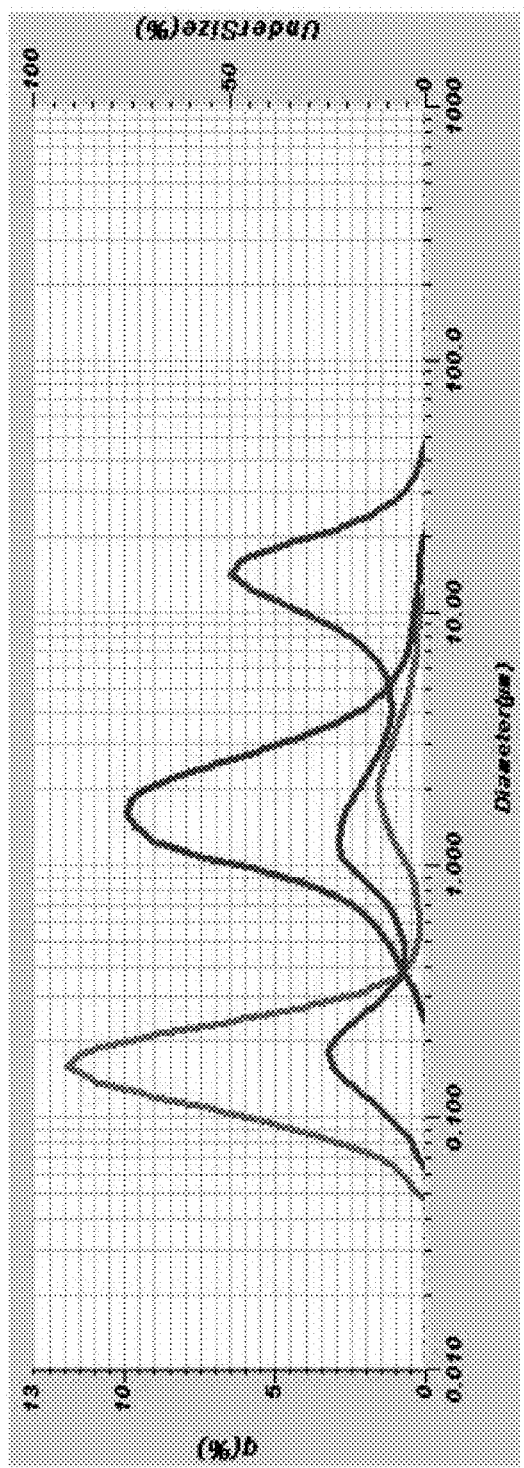
FIG. 16 shows laser scattering particle size distribution analysis of amphetamine in ethanol after 40 hours of milling: before drying (median size=170 nm), dried under vacuum and 10 min. sonication (median size=2.91 μm), and dried under vacuum and 30 sec. sonication (median size=1.63 μm).
Figure 17:
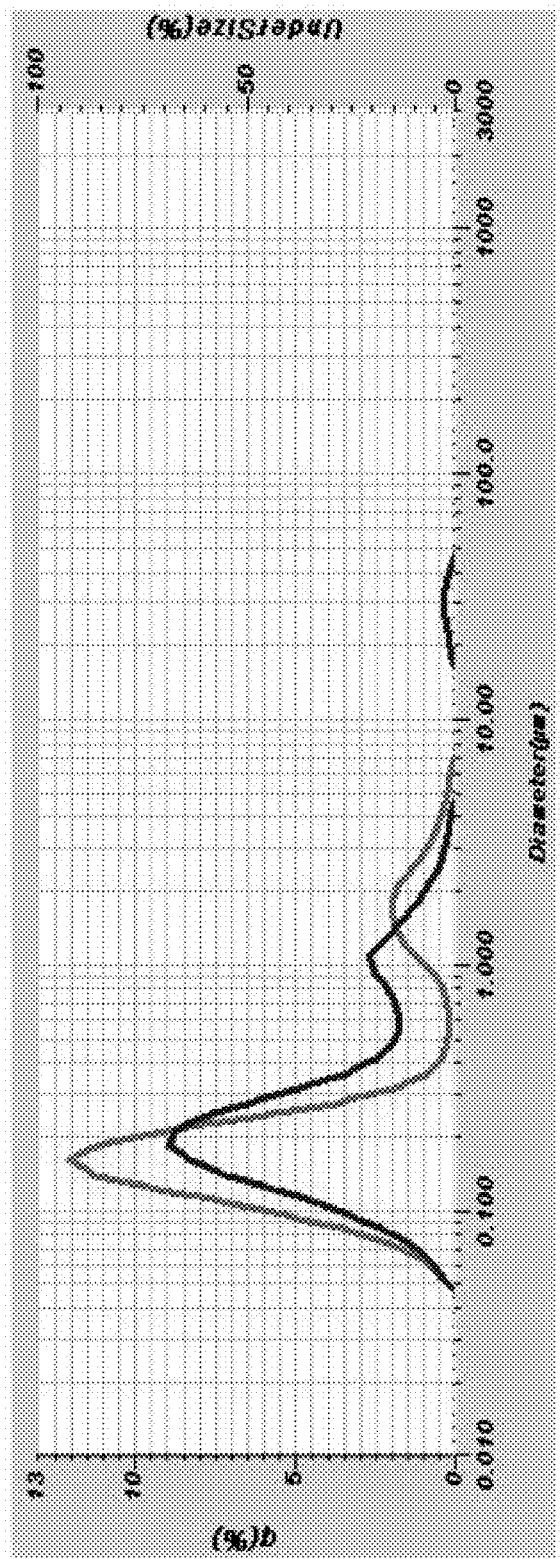
FIG. 17 shows laser scattering particle size distribution analysis of amphetamine in ethanol after 40 hours of milling, before and after lyophilization with PVP cryoprotectant.

Upon successfully milling the amphetamines, experiments were conducted to determine an appropriate drying procedure to maintain the milled particle size. This was tested by redispersing in ethanol and measuring the resultant particle size. First, ethanol was dried off under vacuum, though this resulted in irreversible particle size growth even with sonication to disperse the particles (SEE FIG. 16). It was next attempted to lyophilize the milled dispersion. Lyophilization of the straight suspension was also found to cause an increase in particle size. However, the addition of 1% PVP K-29/32 to the milled suspension as a cryoprotectant was found to adequately maintain particle size. A second larger batch was milled to be used to produce the test article capsules. This batch required 52 hr of milling to eliminate the tail of larger sized particles. Upon completion of the milling, the suspension was harvested and modified with the addition of the PVP K-29/32. The suspension was lyophilized at −45° C./0.1 torr with a cycle time of approximately 17 hr. Post-lyophilized particle size was measured and found to be similar to the pre-lyophilized size (SEE FIG. 17).

Twenty size 000 hard gelatin capsules were filled by hand on a 5-place analytical balance to a target fill of 11.3-11.5 mg. This target fill weight is the calculated equivalent of 6.3 mg of amphetamine in the free base form (See Table 3)

TABLE 3

Calculation of Free-Base Equivalent

| | | |
|---|---|---|
| Yield from Lyophilization | Total Cake Weight | 555 mg |
| | PVP added pre lyophilization | 135 mg |
| | AMP sulfate wt. in cake | 420 mg |
| Free base calculation | AMP sulfate mw | 368.49 |
| | AMP mw | 135.2 |
| | Salt is 2 AMP:1 H2SO4 | 270.4/368.49 |
| | % free-base in salt | 73.38% |
| Free-base target per capsule | 6.3 mg free-base | |
| Salt equivalent | 6.3 mg/0.7338 | 8.59 mg salt |
| Salt % less PVP | 420 mg/555 mg | 75.68% |
| Fill wt. | 8.59 mg/0.7568 | 11.35 mg salt + PVP |

Example 5

Bioanalysis of Nanoparticulates Administered to Subjects

A LC-MS/MS method was developed for the determination of both l-amphetamine and d-amphetamine in mini-pig plasma (sodium heparin) using (d, l)-amphetamine-d6 as an internal standard. Sample volume used was 100 μL of mini-pig plasma, with any necessary dilutions performed in blank mini-pig plasma prior to extraction. Sample clean-up consisted of a liquid-liquid extraction of analyte into methyl tert-butyl ether (MTBE), followed by evaporation of the organic, and reconstitution in mobile phase. The d- and l-isomers of amphetamine were separated by liquid chromatography on a Chiral-CBH column from Chiral Technologies. An isocratic gradient using a mobile phase consisting of 6% acetonitrile in 10 mM ammonium acetate and 50 μM EDTA at 220 μL/min was used to separate l-amphetamine and d-amphetamine, with retention times of approximately 3.6 and 4.6 minutes, respectively, with a total run time of 10 minutes. A calibration curve was prepared by spiking test compound into blank mini-pig plasma with a range from 0.5 ng/mL to 500 ng/mL. timepoints were taken at 15 minutes, 30 minutes, 45 minutes 1 hour, 1.5 hours, 3 hours, 6 hours, 8 hours, and 24 hours. Date indicated that plasma concentrations of d-amphetamine and l-amphetamine in pig plasma peaked prior to the 15 minute timepoint and were being cleared over the first several time-points (e.g., 1.5 hours). For PK analysis, the drug had lower plasma concentrations for both the d- and l-forms of amphetamine. The corresponding PK parameters also reflect this difference in lower AUC. PK analysis demonstrated that both the d- and l-forms of amphetamine were rapidly cleared, and indicated that the peak concentration in plasma occurred prior to the 15 minute time-point. Such rapid clearance was unexpected.

Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of treating ADHD in a subject said method comprising administering to the subject having ADHD a once-daily dose of a pharmaceutical composition, wherein the pharmaceutical composition consists of:
   a. a rapid release component consisting only of dexamphetamine, wherein the dexamphetamine has a mean diameter of up to 50 nm, and a cryoprotectant further wherein the rapid release component is prepared by a process comprising the steps of:
      i) dispersing dexamphetamine in ethanol to generate a dispersed dexamphetamine;
      ii) milling said dispersed dexamphetamine; and
      iii) lyophilizing said dexamphetamine with said cryoprotectant to generate a powdered nanoparticulate dexamphetamine formulation consisting only of said dexamphetamine and said cryoprotectant; and
   b. a delayed release component consisting only of guanfacine.

2. The method of claim 1, wherein said dexamphetamine has a mean diameter of up to 25 nm.

3. The method of claim 1, wherein the cryoprotectant is povidone.

4. The method of claim 1, wherein the rapid release component and the delayed release component are not encapsulated within nanoparticles.

5. A method of treating ADHD in a subject said method comprising administering to the subject having ADHD a once-daily dose of a pharmaceutical composition, wherein the pharmaceutical composition consists of:
   a. a rapid release component consisting only of dexamphetamine, wherein the dexamphetamine has a mean diameter of up to 50 nm;
   b. a cryoprotectant; and
   c. a delayed release component consisting only of guanfacine.

6. The method of claim 5, wherein the dexamphetamine has a mean diameter of up to 25 nm.

* * * * *